(12) United States Patent
Gomi

(10) Patent No.: US 10,006,854 B2
(45) Date of Patent: Jun. 26, 2018

(54) MEASUREMENT DEVICE AND PRINTING APPARATUS

(71) Applicant: Seiko Epson Corporation, Tokyo (JP)

(72) Inventor: Tsugio Gomi, Fujimi (JP)

(73) Assignee: Seiko Epson Corporation (JP)

( * ) Notice: Subject to any disclaimer, the term of this patent is extended or adjusted under 35 U.S.C. 154(b) by 0 days. days.

(21) Appl. No.: 15/299,780

(22) Filed: Oct. 21, 2016

(65) Prior Publication Data
US 2017/0122864 A1 May 4, 2017

(30) Foreign Application Priority Data
Oct. 28, 2015 (JP) ................. 2015-212278

(51) Int. Cl.
| | |
|---|---|
| *B41J 29/38* | (2006.01) |
| *G01N 21/25* | (2006.01) |
| *G01N 21/27* | (2006.01) |
| *B41J 11/00* | (2006.01) |
| *G01J 3/46* | (2006.01) |
| *G01N 21/31* | (2006.01) |

(52) U.S. Cl.
CPC ........ *G01N 21/251* (2013.01); *B41J 11/0095* (2013.01); *B41J 29/38* (2013.01); *G01J 3/46* (2013.01); *G01N 21/27* (2013.01); *G01N 21/31* (2013.01); *G01N 2201/062* (2013.01); *G01N 2201/068* (2013.01); *G01N 2201/0612* (2013.01); *G01N 2201/0633* (2013.01)

(58) Field of Classification Search
CPC ........ B41J 2/01; B41J 11/0095; B41J 29/393; G01N 2201/062; G01N 2201/068; G01N 21/27; G01N 21/251; G01N 2201/0612; G01N 2201/0633
USPC .......................................... 347/19
See application file for complete search history.

(56) References Cited

FOREIGN PATENT DOCUMENTS

JP        2005-059552 A        3/2005

*Primary Examiner* — Jannelle M Lebron
(74) *Attorney, Agent, or Firm* — Harness, Dickey & Pierce, P.L.C.

(57) ABSTRACT

A spectrometer includes a light source that radiates illumination light, and a measurement unit that measures measurement light in which illumination light is reflected by a medium. In a case where an illumination region that is a region in which the medium is irradiated with illumination light is smaller than a measurement region that is a region of the medium measurable by the measurement unit and in which the movement of the medium in the direction is within a range of an acceptable fluctuation amount, the illumination region is included in the measurement region.

9 Claims, 25 Drawing Sheets

FIG. 12
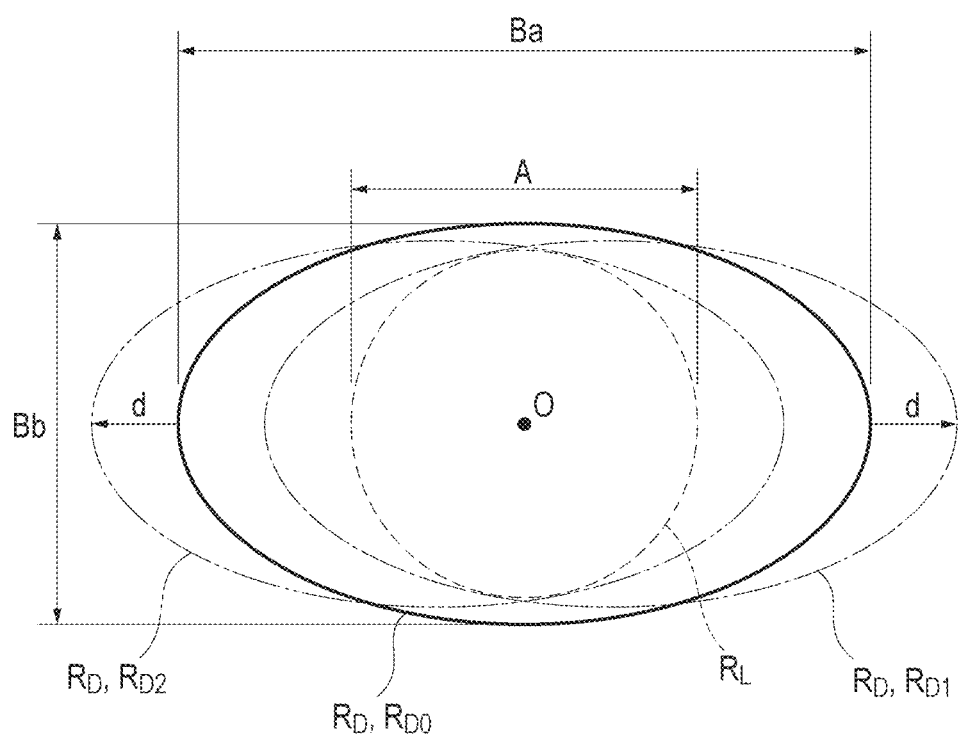
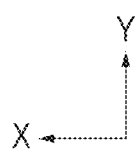

MEASUREMENT DEVICE AND PRINTING APPARATUS

BACKGROUND

1. Technical Field

The present invention relates to a measurement device, a printing apparatus, and the like.

2. Related Art

In image forming apparatuses, such as a printer, in the related art, a device provided with a colorimetry device that measures the color of a measurement object is known (for example, JP-A-2005-59552).

The device disclosed in JP-A-2005-59552 is provided with a light source that radiates an illumination light on the measurement object, and measures the light reflected by the light source with a measuring device. The device disclosed in JP-A-2005-59552 includes a focal position of the illumination light that is set behind (opposite side to the measuring device) of the measurement object. In this case, the fluctuation amount in the light intensity of light received by the measuring device can be reduced and lowering of the measurement precision can be suppressed, even in a case where swelling (cockling) or the like arises due to the influence of humidity or temperature or the action of physical external forces.

Incidentally, in a case of performing colorimetry with a colorimeter, colorimetry is ordinarily carried out according to geometric conditions stipulated by the colorimetry standards (JIS Z 8722), that is, the measurement object is irradiated with illumination light at 45 degrees and the reflection light reflected at 90 degrees is measured by the measuring device (45/0° colorimetry system), the measurement object is irradiated with illumination light at 90 degrees and the reflection light reflected at 45 degrees is measured by the measuring device (0/45° colorimetry system).

In this case, in a case where cockling or the like arises in the measurement object, and the position of the measurement object fluctuates, the distance between the measurement object, the colorimeter, and the light source fluctuates. Therefore, the position of the illumination region at which the measurement object is irradiated with illumination light or the measurement region able to be measured with the measuring device fluctuates. For example, although the measurement region does not fluctuate in the 45/0° colorimetry system, the illumination region moves in a direction separating with respect to the light source according to the displacement direction of the position of the measurement object. Additionally, although the illumination region does not fluctuate in the 0/45° colorimetry system, the measurement region moves in a direction separating with respect to the colorimeter.

In this way, when the illumination region or the measurement region move, because the light quantity of illumination light fluctuates in the portion where the measurement region and the illumination region are superimposed, a problem arises where the light quantity of the measurement light incident on the measuring device also fluctuates and it is difficult to carry out colorimetry with high precision.

SUMMARY

An advantage of some aspects of the invention is to provide a measurement device and a printing apparatus capable of high precision measurement.

According to an application example of the invention, there is provided a measurement device including a light source that radiates an illumination light; and a measurement unit that measures measurement light that is reflection light obtained by reflecting illumination light by a measurement object or transmitted light obtained by passing the illumination light through the measurement object, in which an illumination region that is a region in which the measurement object is illuminated by the illumination light is smaller than a measurement region that is the region of the measurement object measurable by the measurement unit, and is included in the measurement region.

In the application example, the region (illumination region) in which the measurement object is irradiated with illumination light from the light source is smaller than the region (measurement region) of the measurement object that is measurable by the measurement unit, and is included in the measurement region.

In the configuration, even in a case where the position of the measurement object moves along the normal direction of the surface of the measurement object due to cockling or the like and the distance between the measurement object and the measurement device fluctuates, fluctuations in the total light quantity of the measurement light incident on the measurement unit are suppressed by positioning the illumination region within the measurement region. Accordingly, high precision measurement can be carried out even in a case where a distance fluctuation arises between the measurement object and the measurement device.

In the measurement device of the application example, it is preferable that an illumination direction of the illumination light toward the measurement object is different to a measurement direction of the measurement light toward the measurement unit.

In the application example, the illumination direction and the measurement direction are different. For example, in a case where the illumination light is radiated from the normal direction of the measurement object, and the measurement light reflected in the normal direction is measured with the measurement unit, the specular reflection component is included in the measurement light, and the measurement precision is lowered, particularly in a case of performing colorimetry or the like. In contrast, because the illumination direction and the measurement direction are different in the application example, the specular reflection component included in the measurement light is reduced, and improvements in the measurement precision are achieved.

In the measurement device of the application example, it is preferable that an angle formed between a normal line of a surface of the measurement object and a main light beam of the illumination light is $\theta$, the angle formed between the normal line of the surface of the measurement object and the main light beam of the measurement light be $\phi$, the distance between one end of the illumination region and the other end is A, the distance between one end of the measurement region and the other end is B, and the acceptable fluctuation amount of the measurement object from a predetermined reference position with respect to the normal line of the surface of the measurement object is d, and in a case where a surface orthogonal to the normal line that passes through the origin point is a reference plane, the point that is the distance of $d \tan \theta$ from the origin point to the light source projection position side on a first straight line that joins the origin point from the light source projection position on which the light source is projected on the reference plane is the first point, the point that is the distance of $d \tan \phi$ from the origin point to the measurement unit projection position side on a second straight line that joins the origin point from the measurement unit projection position on which the measurement unit is projected on the reference plane is the second point and the first straight line, the angle formed between a third straight line that joins the first point and the second point is α, and the angle formed between the third straight line and the second straight line is β, in plan view taken along the normal line of the surface of the measurement object where the main light beam of the illumination light and the main light beam of the measurement light cross at an origin point in a case where the measurement object is positioned at the reference position $$B \geq A+2d(\tan \phi \cos \beta + \tan \theta \cos \alpha)$$

is satisfied.

For example, in the 0/45° colorimetry system or the 45/0° colorimetry system, because α=β=0°, and (θ,φ)=(0°, 45°) or (45°, 0°), B≥A+2d is satisfied.

In the application example, by satisfying the above conditions, as long as the fluctuation amount is within the acceptable fluctuation amount d, the illumination region is included in the measurement region even in a case where the movement of the measurement object moves in the normal direction. Therefore, even if the distance between the measurement object and the measurement device fluctuates, fluctuations in the total light quantity measured by the measurement unit can be suppressed and improvements in the measurement precision are achieved, as long as the fluctuation amount is within the acceptable fluctuation amount.

In the measurement device of the application example, it is preferable that the measurement region is an ellipse.

In the application example, the measurement region is an ellipse. In a case where the size of the measurement region is large, stray light and the like easily enter the measurement unit, and there are cases where the measurement precision is lowered.

Meanwhile, if the shape of the measurement region is made an ellipse in which the relative movement direction of the illumination region with respect to the measurement region when the position of the measurement object is made the long axis, the illumination region can be included in the measurement region, even in a case where fluctuations in the measurement object arise. Since the area of the region can be reduced compared to a case where the measurement region is circular, the influence of stray light can be suppressed, and further improvements in the measurement precision are achieved.

In the measurement device of the application example, it is preferable that the measurement unit includes a concave mirror in which the measurement region is the ellipse.

In the application example, the shape of the measurement region due to the concave mirror provided in the measurement unit is made an ellipse. In this case, the elliptical measurement region can be given a simple structure.

That is, in a configuration in which only light from the elliptical measurement region passes through the measurement unit using a plurality of slits or the like, the measurement light of the elliptical measurement region is incident in the measurement unit as parallel light. In this case, since the shape of the optical path orthogonal to the main light beam of the measurement light is made the same shape and same size as the measurement region, it is necessary to also use a light receiving unit with the same size. Although a configuration can be used in which the measurement light is collected on the light receiving unit by a lens or the like, the number of components increases when a lens is disposed in addition to the slits, and the configuration increases in complexity. In contrast thereto, in the application example, the measurement region can be made an ellipse with a single concave mirror, and light from the measurement region can be collected with respect to the light receiving unit by the concave mirror. Thus, the configuration can be further simplified, and size reductions in the measurement device can be promoted.

According to another application example of the invention, there is provided a measurement device including a light source that radiates an illumination light; and a measurement unit that measures measurement light that is reflection light obtained by reflecting illumination light by a measurement object or transmitted light obtained by passing the illumination light through the measurement object, in which a measurement region that is a region of measurement object measurable by the measurement unit is smaller than an illumination region in which the measurement object is irradiated with illumination light, and is included in the illumination region.

In the application example, the measurement region is smaller than the illumination region, and is included in the illumination region. In such a configuration, if the illumination region is irradiated with uniform light, the changes in the light quantity of the measurement light incident on the measurement unit can be reduced even in a case where the position of the measurement region is moved within the illumination region according to fluctuations or the like in the position of the measurement object. Accordingly, high precision measurement can be performed, even in a case where a distance fluctuation arises between the measurement object and the measurement device.

It is preferable that the measurement device of the above-described application examples further includes a distance measurement unit that measures a distance between the measurement object and the measurement unit; and a correction unit that corrects a measured value measured by the measurement unit based on the distance measured by the distance measurement unit.

In the application example, the distance between the measurement object and the measurement unit is measured by the distance measurement unit, and the correction unit corrects the measured value based on the measured distance. Accordingly, measurement with higher precision can be carried out by correcting the measured value in response to the distance, even in a case where the distance between the measurement object and the measurement unit fluctuates.

In the measurement device of the application example, it is preferable that correction unit acquires distance-light quantity data in which a light quantity fluctuation amount with respect to the distance between the measurement object and the measurement unit is recorded, and corrects the measured value based on the distance-light quantity data.

In the application example, distance-light quantity data in which the light quantity fluctuation amount with respect to the distance is recorded is acquired. Therefore, the light quantity fluctuation amount with respect to the measured distance can be easily acquired, and the measured value can be easily corrected based on the light quantity fluctuation amount.

In the measurement device of the application example, it is preferable that the measurement unit includes a spectral element that divides light with a predetermined wavelength from the measurement light.

In the application example, colorimetry can be carried out on the measurement object or an image formed on the measurement object by measuring the light divided by the spectral element.

It is preferable that the measurement device of the application example further includes a carriage on which the light source and the measurement unit are mounted; and a movement mechanism that causes the carriage to move relative to the measurement object.

In the application example, measurement can be carried out on the measurement object of a region following one direction by the colorimeter being moved relative to the one direction of the measurement object.

According to still another application example of the invention, there is provided a printing apparatus including the above-described measurement device, and an image forming unit that forms an image on a measurement object.

In the application example, measurement can be carried out with higher precision by the measurement device as described above on an image formed on the measurement object by the image forming unit.

It is preferable that the printing apparatus of the application example includes a carriage on which light source and the measurement unit are mounted, and that the image forming unit is mounted on the carriage.

In the application example, the light source, the measurement unit, and the image forming unit are mounted on the same carriage. In this case, simplification of the configuration of the printing apparatus can be achieved, compared to a case where a carriage on which the image forming unit is mounted and a carriage on which the light source and the measurement unit are mounted are provided.

BRIEF DESCRIPTION OF THE DRAWINGS

The invention will be described with reference to the accompanying drawings, wherein like numbers reference like elements.

FIG. 12 is a drawing illustrating the positional relationship of the measurement region and the illumination region when the medium is viewed from the normal direction in the modification example of the second embodiment.

FIG. 21 is viewed from the normal direction of the medium.

DESCRIPTION OF EXEMPLARY EMBODIMENTS

First Embodiment

Figure 1:
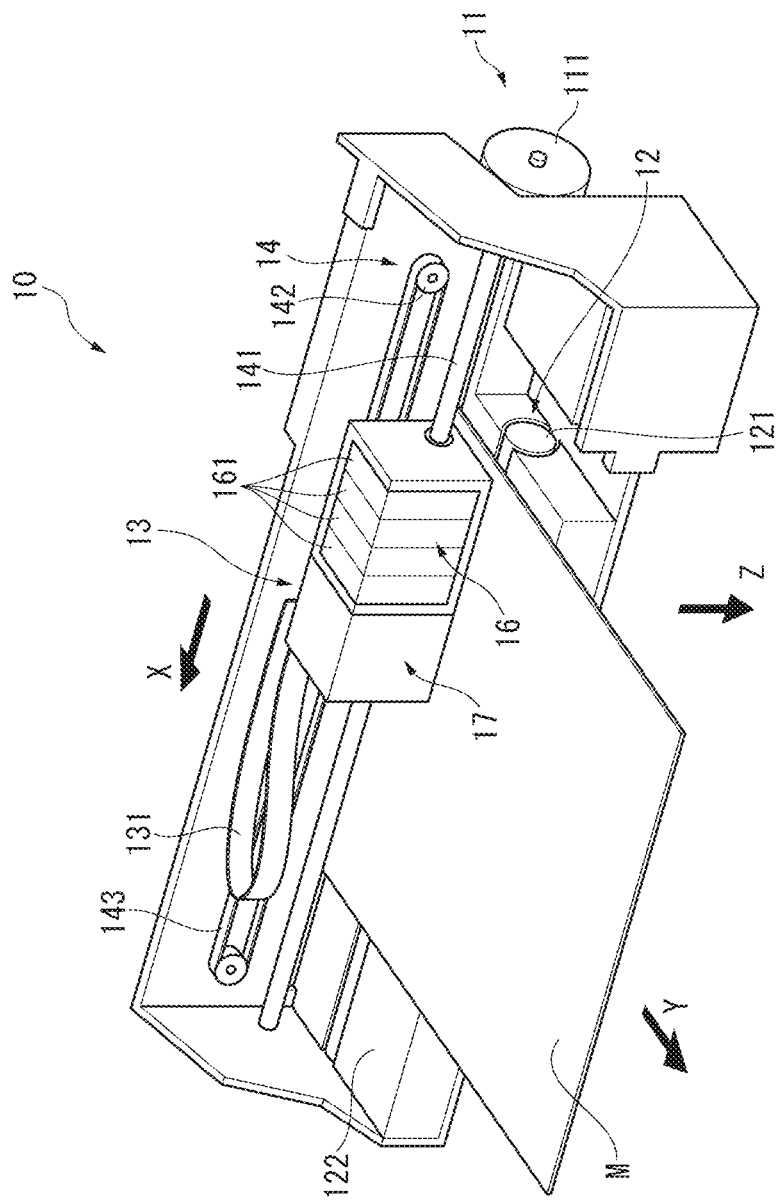
FIG. 1 is a drawing illustrating a schematic configuration of an external appearance of a printer of the first embodiment.
Figure 2:
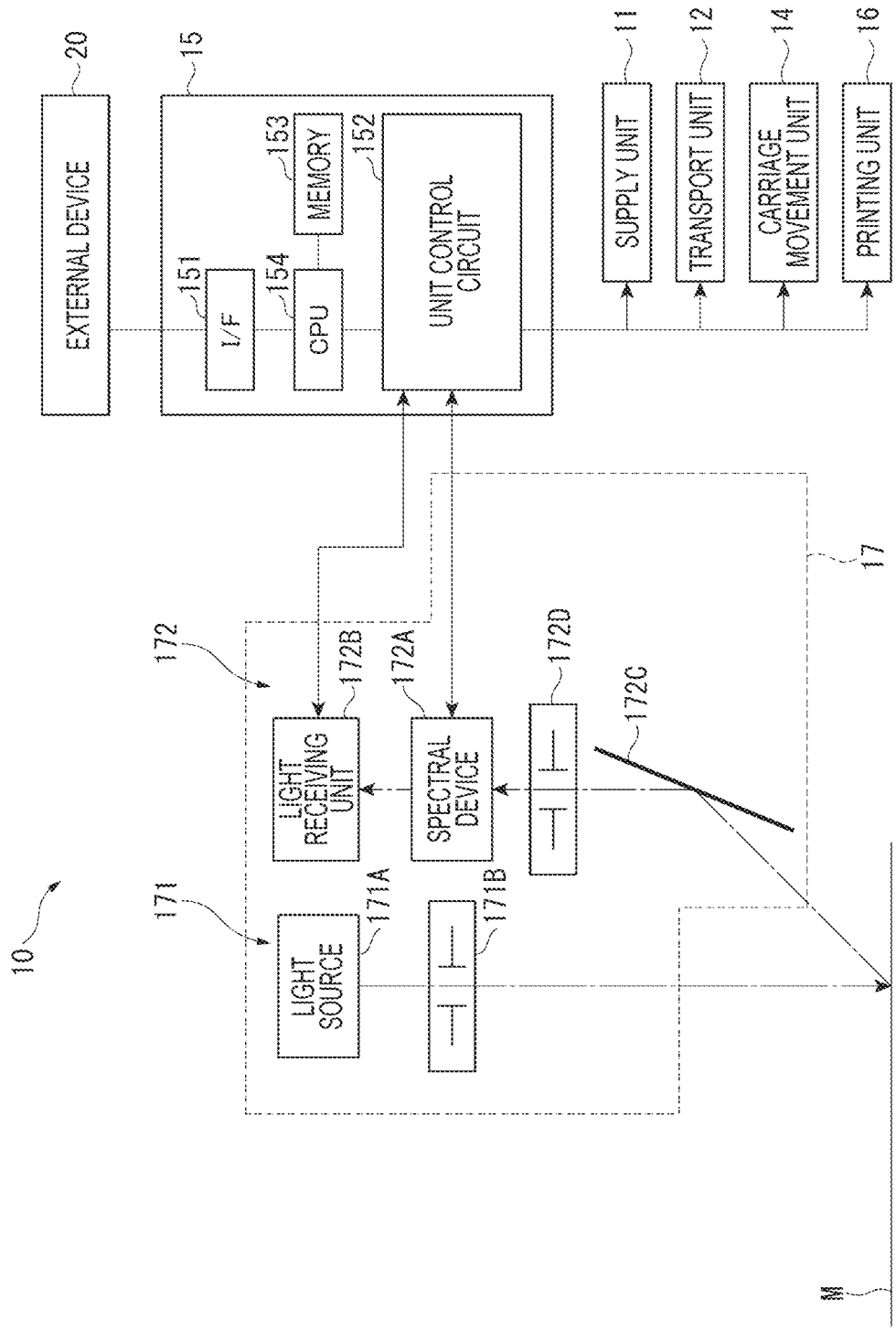
FIG. 2 is a block diagram illustrating a schematic configuration of the printer of the first embodiment.

Below, the first embodiment according to the invention will be described based on the drawings. In the embodiment, a printer 10 (ink jet printer) provided with the measurement device will be described below as an example of the printing apparatus of the invention.
Schematic Configuration of Printer FIG. 1 is a drawing illustrating a schematic configuration of the external appearance of the printer 10 of the first embodiment. FIG. 2 is a block diagram illustrating a schematic configuration of the printer 10 of the embodiment.

As illustrated in FIG. 1, the printer 10 is provided with a supply unit 11, a transport unit 12, a carriage 13, a carriage movement unit 14, and a control unit 15 (refer to FIG. 2). The printer 10 controls each unit 11, and 14, and the carriage 13 and prints an image on a medium M (measurement object of the invention) based on printing data input from an external device 20, such as a personal computer. The printer 10 of the embodiment forms a color patch for colorimetry at a predetermined position on the medium M based on printing data for calibration that is set in advance and performs spectroscopic measurement on the color patch. Accordingly, the printer 10 compares the actual measured value with respect to the color patch and the printing data for calibration, determines whether there is a color shift in the printed color, and performs color correction base on the actual measured value in a case where there is a color shift.

Below, each configuration of the printer 10 will be specifically described.

The supply unit 11 is a unit that supplies a medium M (in the embodiment, a white sheet is given as an example) that is an image formation object to an image forming position. The supply unit 11 is provided with a roll member 111 on which the medium M is wound (refer to FIG. 1), a roll driving motor (not shown) and a roll drive wheel train (not shown) and the like. The roll driving motor is driven to rotate based on instructions from the control unit 15, and rotational power of the roll driving motor is transmitted to the roll member 111 via the roll drive wheel train. Accordingly, the roll member 111 rotates, and the sheet wound on the roll member 111 is supplied to the downstream side (+Y direction) in the Y direction (sub-scanning direction).

It should be noted that although an example in which the sheet wound on the roll member 111 is supplied is illustrated in the embodiment, there is no limitation thereto. For example, the medium M may be supplied by any supply method, such as supplying the media M, such a sheet stacked on a tray or the like, one at a time with a roller or the like.

The transport unit 12 transports the medium M supplied from the supply unit 11 along the Y direction. The transport unit 12 is formed including a transport roller 121, a driven roller (not shown) that is arranged interposing a medium M with the transport roller 121 and that is driven by the transport roller 121, and a platen 122.

When the driving power is transmitted from the transport motor, not shown, and the transport motor is driven according to the control of the control unit 15, the transport roller 121 is driven to rotate by the rotational power and transports the medium M along the Y direction in a state where pinched with the driven roller. A platen 122 that faces the carriage 13 is provided on the downstream side (+Y side) in the Y direction of the transport roller 121.

The carriage 13 is provided with a printing unit 16 that prints an image on the medium M and a spectrometer 17 that performs spectroscopic measurement of a predetermined measurement position (measurement region) on the medium M.

The carriage 13 is provided to be movable along the main scanning direction (X direction) that intersects the Y direction by a carriage movement unit 14.

The carriage 13 is connected to the control unit 15 by the flexible circuit 131, and carries out the printing process with the printing unit 16 (image forming process with respect to the medium M) and the light quantity measurement process with the spectrometer 17 based on instruction from the control unit 15.

The detailed configuration of the carriage 13 will be described later.

The carriage movement unit 14 forms a movement mechanism in the invention, and causes the carriage 13 to reciprocate along the X direction based on instructions from the control unit 15.

The carriage movement unit 14 is formed including a carriage guide shaft 141, a carriage motor 142, and a timing belt 143.

The carriage guide shaft 141 is arranged along the X direction, and both end portions are fixed to the housing of the printer 10. The carriage motor 142 causes the timing belt 143 to be driven. The timing belt 143 is supported to be substantially parallel to the carriage guide shaft 141, and is fixed to one portion of the carriage 13. When the carriage motor 142 is driven based on the instructions of the control unit 15, the timing belt 143 is run forward, and the carriage 13 fixed to the timing belt 143 reciprocates guided on the carriage guide shaft 141.

Next, the configuration of the printing unit 16 provided on the carriage 13 and the spectrometer 17 will be described.

Configuration Printing Unit (Image Forming Unit)

The printing unit 16 is the image forming unit of the invention and individually discharges ink on the medium M at a portion that faces the medium M and forms an image on the medium M.

The printing unit 16 has ink cartridges 161 corresponding to a plurality of colors of ink that are mounted to be freely detachable, and the ink is supplied via a tube (not shown) from each ink cartridge 161 to an ink tank (not shown). Nozzles (not shown) that discharge ink droplets are provided in the lower surface (position facing the medium M) of the printing unit 16 corresponding to each color. A piezoelectric element is arranged in the nozzles, and an ink droplet that is supplied from the ink tank is discharged by the piezoelectric element being driven and lands on the medium M, thereby forming a dot.

Configuration of Spectrometer

The spectrometer 17 corresponds to the measurement device of the invention and is provided with a light source unit 171 and a measurement unit 172 as illustrated in FIG. 2.

The spectrometer 17 radiates illumination light from the light source unit 171 onto the medium M, and the reflection light reflected by the medium M is received by the measurement unit 172. The spectral device 172A provided in the measurement unit 172 is capable of selecting a transmitted wavelength based on control of the control unit 15, and is capable of spectroscopic measurement of the medium M by measuring the light quantity of light for each wavelength in visible light.

It should be noted that spectroscopic measurement in the embodiment is carried out according to the format (0/45° colorimetry system) of the optical geometric conditions stipulated by the colorimetry standard (JIS Z 8722). That is, in the embodiment, the illumination light from the light source unit 171 is made incident on the normal direction (angle of incidence of 10° or less) with respect to the medium M, and the light reflected at 45°±2° by the medium M is received by the measurement unit 172. That is, the illumination direction of illumination light toward the medium M and the measurement direction of measurement light toward the measurement unit 172 are different.

It should be noted that, in the embodiment, although a configuration in which the light source unit 171 and the measurement unit 172 are lined up following the X direction is given for convenience of description, there is no limitation thereto, and a configuration in which the light source unit 171 and the measurement unit 172 are lined up following the Y direction may be used, or a configuration in which the light source unit 171 and the measurement unit 172 are lined up along a direction that intersects the XY direction may be used.

Configuration of Light Source Unit

As illustrated in FIG. 2, the light source unit 171 is provided with a light source 171A and an illumination optical member 171B that guides illumination light radiated from the light source 171A onto the medium M.

The light source 171A is a member that generates illumination light that is radiated on to the medium M. In the embodiment, the configuration includes a spectrometer 17 mounted on the carriage 13 of the printer 10, and it is necessary to reduce the size and weight of the spectrometer 17. Therefore, it is preferable to use an LED or LD (semiconductor laser) or the like as the light source 171A.

The illumination optical member 171B emits illumination light radiated from the light source 171A toward the medium M, and forms the illumination region $R_L$ (refer to FIGS. 5 and 6) on the medium M. The illumination optical member 171B is formed by a single or a plurality of optical members. For example, a configuration in which a single or a plurality of apertures is provided as the illumination optical member 171B, and illumination light with a predetermined optical path diameter passing through the apertures is radiated on the medium M is a possible example. A spot light can be radiated on the illumination region $R_L$ on the medium M by providing such apertures.

A collimator lens may be further provided as the illumination optical member 171B. In this case, illumination light parallel to the medium M can be radiated from the light source unit 171. Thus, the size (spot diameter) of the illumination region $R_L$ on the medium M does not change, even in a case where the position of the medium M is displaced in the Z direction.

It should be noted that a configuration may be used in which a collecting lens by which the illumination light is collected on the measurement position of the medium M is provided as an illumination optical member 171B. In this case, when positioned at the reference position at which the distance between the medium M and the spectrometer 17 becomes a predetermined reference distance, it is preferable that the illumination light is matched to the focal position of the collection lens to be collected on point of the medium M.

Configuration of Measurement Unit

The measurement unit 172 is formed by a spectral device 172A, a light receiving unit 172B, a reflecting mirror 172C, a light receiving optical member 172D, and the like, as illustrated in FIG. 2.

In such a measurement unit 172, the light reflected by the medium M is reflected to the spectral device 172A by the reflecting mirror 172C or the light receiving optical member 172D, and light with a predetermined wavelength divided by the spectral device 172A is received by the light receiving unit 172B.

The light receiving optical member 172D is formed by a single or a plurality of optical members. It should be noted that although FIG. 2 illustrates an example in which the light receiving optical member 172D is provided between the reflecting mirror 172C and the spectral device 172A, there is no limitation thereto. The light receiving optical member 172D may be provided on the optical path as far as the measurement light is received in the light receiving unit 172B, and, for example, may be provided at any of between spectral device 172A and the light receiving unit 172B, between the spectral device 172A and the reflecting mirror 172C, and between the reflecting mirror 172C and a light incidence hole (not shown) in the measurement unit 172 or a plurality of locations.

A single or a plurality of apertures are a possible example of the light receiving optical member 172D. It is possible for the measurement light reflected by the predetermined measurement region $R_D$ (refer to FIGS. 5 and 6) on the medium M to be guided to the spectral device 172A and the light receiving unit 172B by providing such apertures. Although the details are described later, the measurement region $R_D$ in the embodiment has a larger size than the illumination region $R_L$ and the illumination region $R_L$ is included in the measurement region $R_D$.

A lens that collects the measurement light from the measurement region $R_D$ on the light receiving unit 172B and the like may be further provided as the light receiving optical member 172D. If such a lens is used, it is possible to collect the light from the predetermined measurement region $R_D$ on the light receiving unit 172B eve in a case where the aperture and the like are not provided. That is, a measurement region $R_D$ with a desired size can be formed by the light receiving optical member 172D.

Furthermore, a configuration may be used in which a band pass filter is provided as the light receiving optical member 172D and the light other than visible light is cut by the band pass filter.

It should be noted that although size reductions in the measurement unit 172 are achieved in the embodiment by measurement light being reflected by the reflecting mirror 172C, there is no limitation thereto, and a configuration may be used where the measurement light from the medium M is directly incident on the spectral device 172A or the light receiving unit 172B without providing the reflecting mirror 172C.

Configuration of Spectral Device

Figure 3:
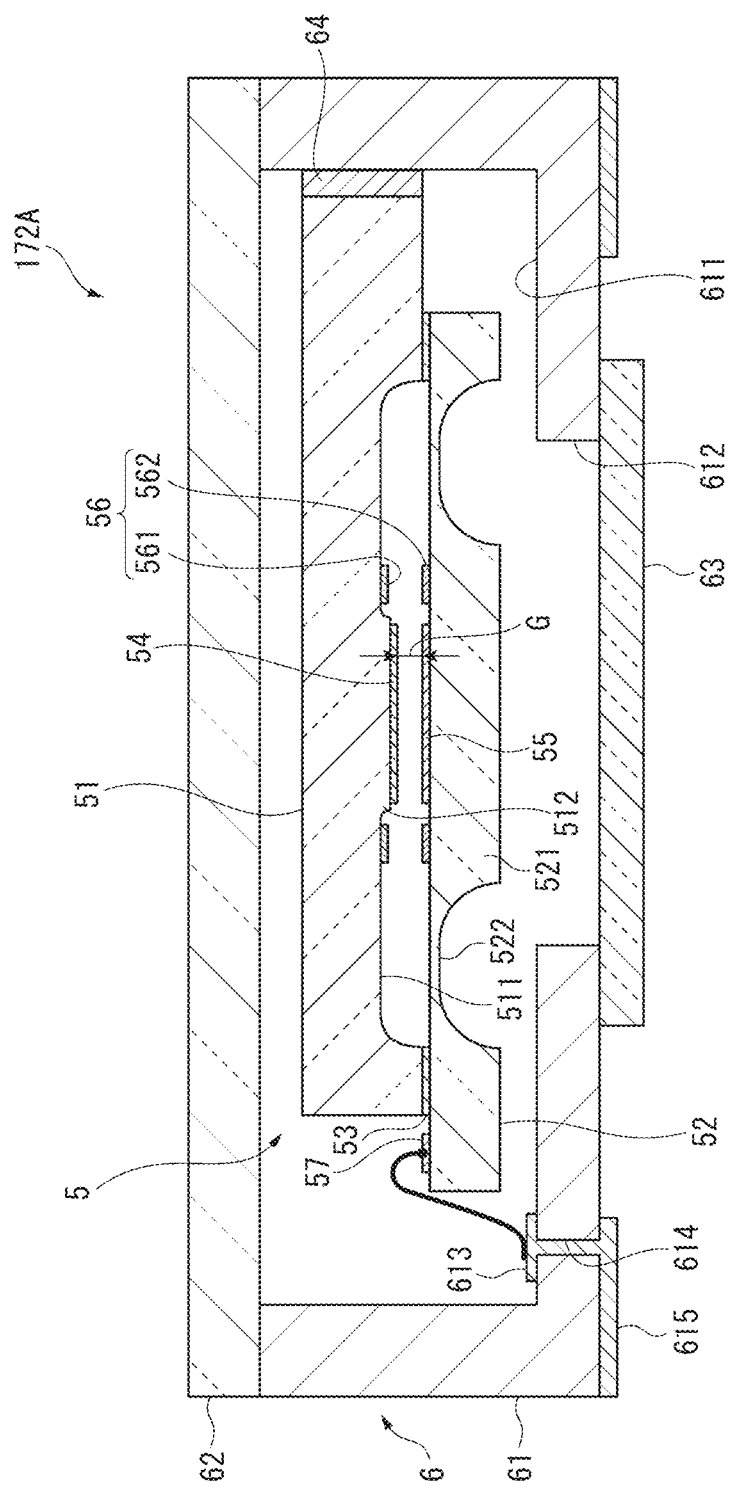
FIG. 3 is a cross-sectional view illustrating a schematic configuration of a spectral device of the first embodiment.

FIG. 3 is a cross-sectional view illustrating a schematic configuration of the spectral device 172A.

The spectral device 172A is provided with a housing 6, and a variable wavelength interference filter 5 (spectral element) housed inside the housing 6.

Configuration of Variable Wavelength Interference Filter

The variable wavelength interference filter 5 is a variable wavelength-type Fabry-Perot etalon element, and forms the spectral element in the invention. Although an example is illustrated in the embodiment in which the variable wavelength interference filter 5 is disposed in the spectrometer 17 in a state where accommodated in the housing 6, a configuration may be used where the variable wavelength interference filter 5 is directly disposed in the spectrometer 17.

The variable wavelength interference filter 5 is provided with a fixed substrate 51 and a movable substrate 52 that has transmissivity to visible light, as illustrated in FIG. 3, and the fixed substrate 51 and movable substrate 52 are integrally formed by being bonded with a bonding film 53. A first groove portion 511 and a second groove portion 512 with a shallower groove depth than the first groove portion 511 are provided on the fixed substrate 51, and a fixed electrode 561 and fixed reflection film 54 are provided on the first groove portion 511 and the second groove portion 512, respectively. The fixed reflection film 54 is formed by a metal film such as Ag, an alloy film, such as an Ag alloy, a dielectric multilayer film in which a high refraction film and a low refraction film are stacked or a stacked body in which the metal film (alloy film) and the dielectric multilayer film are stacked.

The movable substrate 52 is provided with a movable portion 521, and a holding portion 522 that is provided outside the movable portion 521 and that holds the movable portion 521. A movable electrode 562 that faces the fixed electrode 561 and a movable reflection film 55 that faces the fixed reflection film 54 are provided on the surface that faces the fixed substrate 51 of the movable portion 521. A reflection film with the same configuration as the above-described fixed reflection film 54 is used as the movable reflection film 55. The holding portion 522 is a diaphragm that surrounds the periphery of the movable portion 521, and is formed with the thickness dimensions smaller than the movable portion 521.

The gap dimensions of the gap G between the fixed reflection film 54 and the movable reflection film 55 can be changed in such a variable wavelength interference filter 5 by forming the electrostatic actuator 56 by the fixed electrode 561 and the movable electrode 562 and applying a voltage to the electrostatic actuator 56. A plurality of electrode pads 57 that are individually connected to the fixed electrode 561 or the movable electrode 562 are provided on the outer peripheral portion (region not facing the fixed substrate 51) of the movable substrate 52.

Configuration of Housing

The housing 6 is provided with a base 61 and a glass substrate 62, as illustrated in FIG. 3. The base 61 and the glass substrate 62 are formed with an accommodation space in the interior by being bonded by means of a low melting point glass bonding or the like, and the variable wavelength interference filter 5 is accommodated in the accommodation space.

The base 61 is formed by stacking thin plate-like ceramics, and includes a recessed portion 611 capable of accommodating the variable wavelength interference filter 5. The variable wavelength interference filter 5 is fixed, for example, the side surface of the recessed portion 611 of the base 61 by a fixing material 64. A light through hole 612 is provided in the bottom surface of the recessed portion 611 of the base 61, and a cover glass 63 that covers the light through hole 612 is bonded thereto.

An inside terminal portion 613 that is connected to the electrode pad 57 of the variable wavelength interference filter 5 is provided on the base 61 and the inside terminal portion 613 is connected to an outside terminal portion 615 provided on the outside of the base 61 via a conducting hole 614. The outside terminal portion 615 is electrically connected to the control unit 15.

Configuration of Light Receiving Unit

Returning to FIG. 2, the light receiving unit 172B is disposed on the optical axis (on the straight line that passes through the center points of the reflection films 54 and 55) of the variable wavelength interference filter 5, receives light passing through the variable wavelength interference filter 5 in the light receiving region, and outputs a detection signal (current value) in response to the amount of received light. The detection signal output by the light receiving unit 172B is input to the control unit 15 via the I-V converter (not shown), amplifier (not shown) and the AD converter (not shown).

Configuration of Control Unit

Next, the control unit 15 will be described.

The control unit 15 is formed including an I/F 151, a unit control circuit 152, a memory 153, and a central processing unit (CPU) 154, as illustrated in FIG. 2.

The I/F 151 inputs printing data input from the external device 20 to the CPU 154.

The unit control circuit 152 is provided with a control circuit that controls each of the supply unit 11, the transport unit 12, the printing unit 16, the light source 171A, the variable wavelength interference filter 5, the light receiving unit 172B, and the carriage movement unit 14, and controls the operation of each unit based on an instruction signal from the CPU 154. It should be noted that the control circuits of each unit are provided separately to the control unit 15 and may be connected to the control unit 15.

The memory 153 stores various programs and a variety of data that control the operation of the printer 10.

Examples of the variety of data include V-λ data that indicates the light that passes through the variable wavelength interference filter 5 with respect to the voltage applied to the electrostatic actuator 56 when controlling the variable wavelength interference filter 5, and printing profile data that stores the discharge amount of each ink with respect to the color data included in the print data. The light emitting characteristics with respect to each wavelength of the light source 171A, the light reception characteristics with respect to each wavelength of the light receiving unit 172B (light receiving sensitivity characteristics), and the like may be stored.

Figure 4:
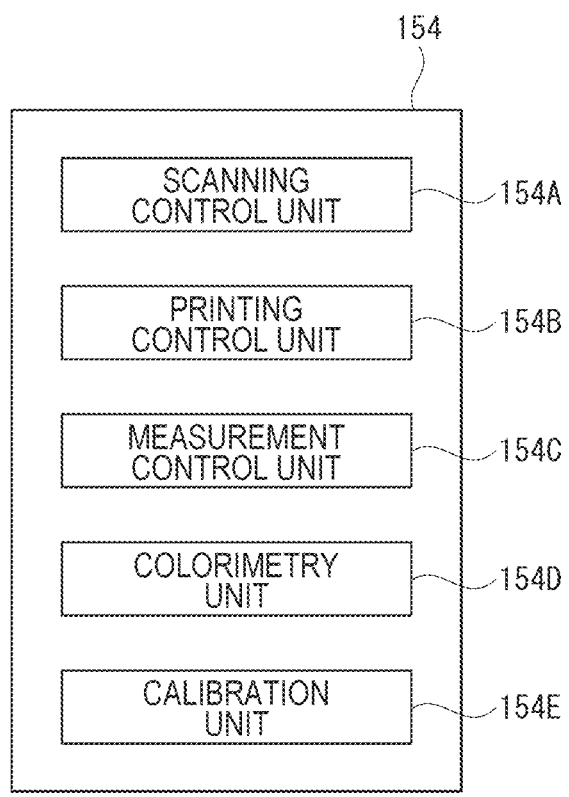
FIG. 4 is a block diagram illustrating a functional configuration of a CPU included in the control unit of the printer of the first embodiment.

FIG. 4 is a block diagram illustrating a functional configuration of a CPU 154 included in the control unit 15 of the printer 10.

The CPU 154 functions as a scanning control unit 154A, a printing control unit 154B, a measurement control unit 154C, a colorimetry unit 154D, a calibration unit 154E, and the like, as illustrated in FIG. 4, by reading out and executing various programs stored in the memory 153.

The scanning control unit 154A outputs an instruction signal indicating the supply unit 11, the transport unit 12, and the carriage movement unit 14 being driven to the unit control circuit 152. Accordingly, the unit control circuit 152 causes the roll driving motor of the supply unit 11 to be driven and the medium M to be supplied to the transport unit 12. The unit control circuit 152 causes the transport motor of the transport unit 12 to be driven and transports a predetermined region of the medium M along the Y direction as far as the position facing the carriage 13 of the platen 122. The unit control circuit 152 causes the carriage motor 142 of the carriage movement unit 14 to be driven and the carriage 13 to be moved along the X direction.

The printing control unit 154B outputs the instruction signal indicating the control of the printing unit 16 to the unit control circuit 152 based on the printing data input from an external device 20. When the instruction signal is input from the printing control unit 154B to the unit control circuit 152, the unit control circuit 152 outputs the printing control signal to the printing unit 16, and causes ink to be discharged to the medium M by a piezoelectric element provided in the nozzle being driven. When carrying out printing, the carriage 13 is moved along the X direction, the dot forming operation that forms a dot by ink being discharged from the printing unit 16 during the movement and the transport operation that transports the medium M in the Y direction are alternately repeated, and an image formed from a plurality of dots is printed on the medium M.

The measurement control unit 154C carries out the spectroscopic measurement process. Specifically, the measurement control unit 154C outputs the instruction signal for controlling the light source 171A to the unit control circuit 152, and causes light to be radiated from the light source 171A.

The measurement control unit 154C reads out the driving voltage for the electrostatic actuator 56 with respect to the wavelength of light caused to pass through the variable wavelength interference filter 5 from the V-λ data of the memory 153 and outputs the instruction signal to the unit control circuit 152. Accordingly, the unit control circuit 152 applies the instructed driving voltage to the variable wavelength interference filter 5 and light with a predetermined transmission wavelength is passed through from the variable wavelength interference filter 5.

The measurement control unit 154C stores the wavelength in the memory 153 associated with the voltage (or the wavelength of light that passes through the variable wavelength interference filter 5 corresponding to the voltage) applied to the electrostatic actuator 56.

The colorimetry unit 154D measures the chromaticity with respect to the measurement region $R_D$ based on the amount of received light with respect to light with a plurality of wavelengths obtained by the spectroscopic measurement process.

The calibration unit 154E corrects (updates) the print profile data based on the colorimetry results by the colorimetry unit 154D.

Relationship Between Illumination Region and Measurement Region

Next, the relationship between the illumination region $R_L$ at which the medium M is illuminated and the measurement region $R_D$ of the medium M by the measurement unit 172 when measurement is carried out with respect to the medium M when the illumination light is radiated on the medium M by the light source unit 171 of the above-described spectrometer 17 will be described.

Figure 5:
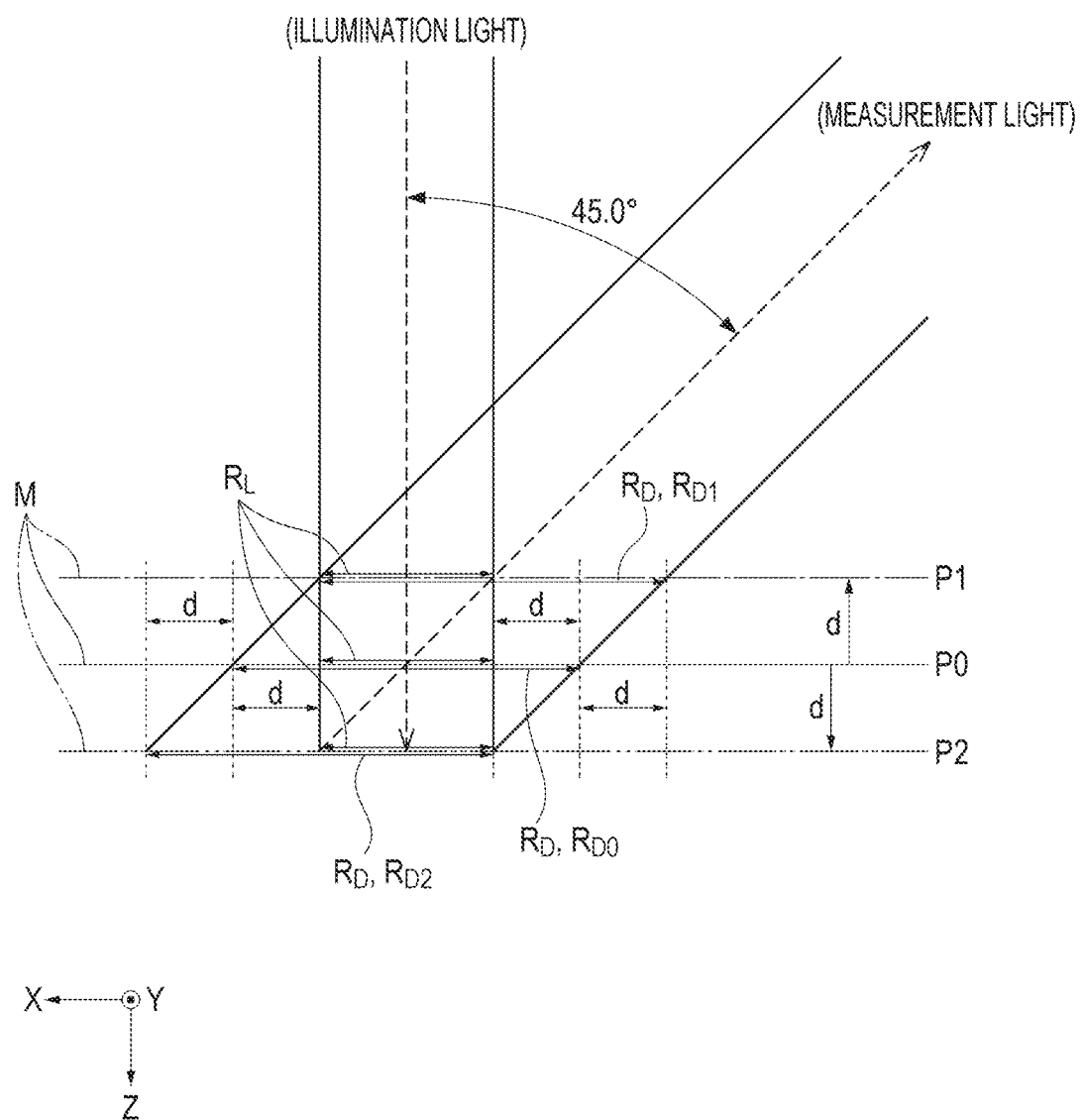
FIG. 5 is a drawing illustrating the position of the measurement region with respect to the illumination region on the XZ plane when the medium is displaced along the normal line in the first embodiment.
Figure 6:
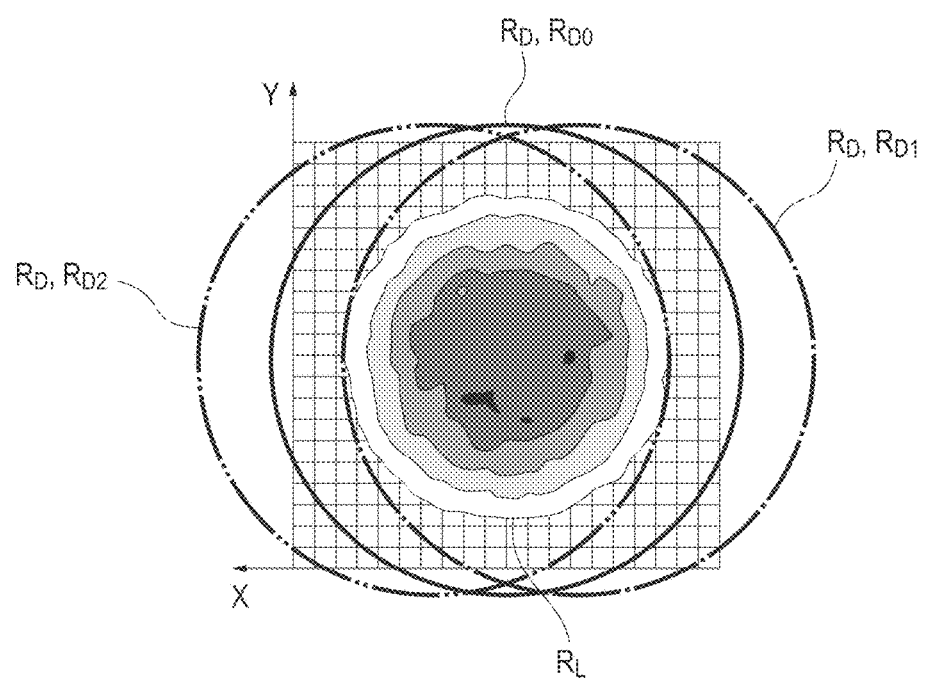
FIG. 6 is a drawing illustrating the position of the measurement region with respect to the illumination region on the XY plane when the medium is displaced along the normal line in the first embodiment.

FIG. 5 is a drawing illustrating the position of the measurement region $R_D$ with respect to the illumination region $R_L$ on the XZ plane when the medium M is displaced along the normal line (Z direction). FIG. 6 is a drawing illustrating the position of the measurement region $R_D$ with respect to the illumination region $R_L$ on the XY plane when the medium M is displaced along the normal line (Z direction).

In the embodiment, an example in which the illumination region $R_L$ and the measurement region $R_D$ are substantially circular is illustrated, as illustrated in FIG. 5.

In the following description, the distance between the medium M and the spectrometer 17 in a case where there is no swelling or the like in the medium M and no displacement of the carriage 13 in the Z direction is the reference distance, and the relative position of the medium M to the spectrometer 17 in this case is the reference position P0.

When performing the colorimetry process (spectroscopic measurement process) with respect to the medium M, there are cases where the distance between the surface of the medium M and the spectrometer 17 fluctuates due to cockling or the like. Although the carriage 13 can move along the X direction by means of the carriage guide shaft 141, there are cases where a portion of the carriage guide shaft 141 is distorted, and the carriage 13 is displaced to the platen 122 side or cases where the carriage is displaced in the Z direction due to vibrations when the carriage 13 moves. Also in this case, the distance between the medium M and the spectrometer 17 fluctuates. It should be noted that, generally, the acceptable value (acceptable fluctuation amount d) of the distance between the medium M and the spectrometer 17 is set in advance in the case of measurement with the spectrometer 17, it is difficult to carryout accurate colorimetry when the distance fluctuates from the reference position P0 in excess of the acceptable fluctuation amount d, and an error is output. Here, the position in a case where the distance between the medium M and the spectrometer 17 becomes smaller than the reference position P0 by the acceptable fluctuation amount d is the first position P1, and the position in a case where the distance between the medium M and the spectrometer 17 is greater than the reference position P0 by the acceptable fluctuation amount d is the second position P2.

In a case where colorimetry is carried out according to the format of the (0/45° colorimetry system) in the optical geometric conditions stipulated by the colorimetry standard (JIS Z 8722), the position of the measurement region $R_D$ is displaced along the X direction when the distance between the medium M and the spectrometer 17 fluctuates. Specifically, when reduced by the distance Δd between the medium M and the spectrometer 17, the measurement region $R_D$ moves by Δd to the −X side. Meanwhile, when increased by the distance Δd between the medium M and the spectrometer 17, the measurement region $R_D$ moves by Δd in the +X side (side separating from the measurement unit 172). Thus, when the medium M moves to the first position P1, the measurement region $R_D$ is the position ($R_{D1}$) moved by d from the position ($R_{D0}$) at the reference position to the −X side. When the medium M moves to the second position P2, the measurement region $R_D$ is the position ($R_{D2}$) moved by d from the position ($R_{D0}$) at the reference position to the +X side.

Figure 7:
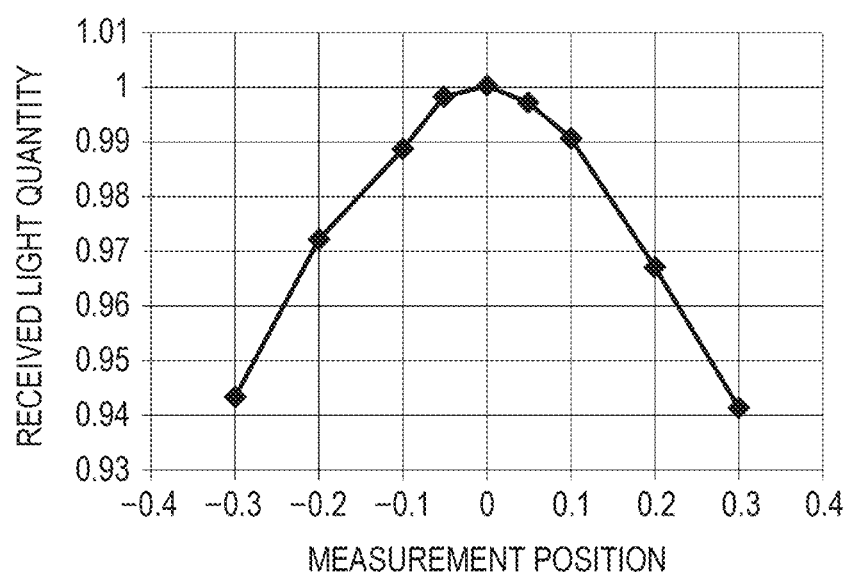
FIG. 7 is a drawing illustrating the total light quantity of light received by the light receiving unit of the measurement unit with respect to the position of the measurement region in the related art example in which the spot diameter of the measurement region and the illumination region are made the same dimension.
Figure 8:
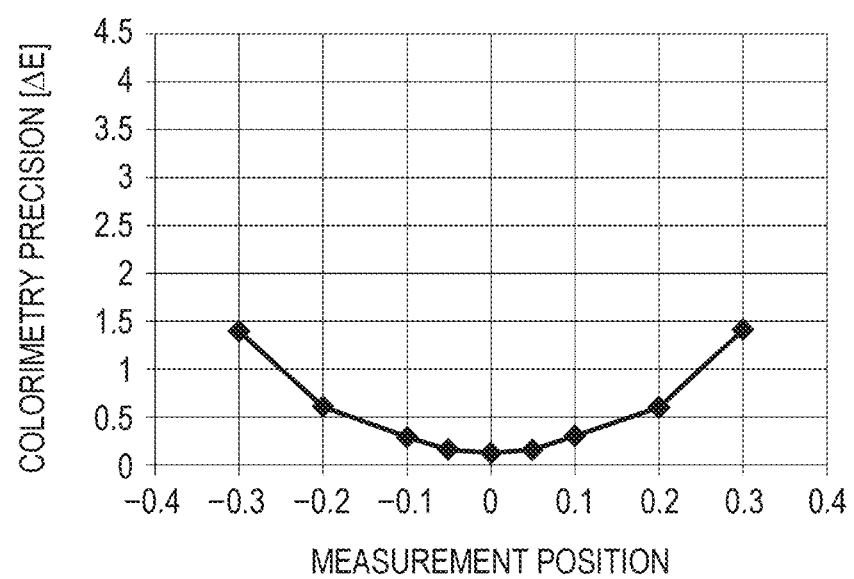
FIG. 8 is a drawing illustrating the measurement results (color difference ΔE) by the spectrometer in the related art example in which the spot diameter of the measurement region and the illumination region are made the same dimension.

FIG. 7 is a drawing illustrating the total light quantity of light received by the light receiving unit 172B of the measurement unit 172 with respect to the position of the measurement region $R_D$ in a case (related art example) where the spot diameter of the measurement region $R_D$ and the illumination region $R_L$ are made the same dimension. FIG. 8 is a drawing illustrating the measurement results (color difference ΔE) by the spectrometer 17 in a case (related art example) where the spot diameter of the measurement region $R_D$ and the illumination region $R_L$ are made the same dimension.

In a case where the spot diameter (distance from one end to the other end of the measurement region $R_D$ along the X direction) of the measurement region $R_D$ and the spot diameter (distance from one end to the other end of the illumination region $R_L$ along the X direction) of the illumination region $R_L$ have the same dimensions, when the relative position of the medium M with respect to the spectrometer 17 moves from reference position P0, since the measurement region $R_D$ moves, and the light quantity of the illumination light radiated on the measurement region $R_D$ is reduced, the total light quantity of light received by the light receiving unit 172B is also reduced, as illustrated in FIG. 7. Accordingly, when colorimetry is carried out by calculating the color difference ΔE based on the measurement results by the spectrometer 17, the colorimetry precision is lowered as illustrated in FIG. 8.

In contrast, the illumination region $R_L$ is included inside the measurement region $R_D$ in the embodiment, even in a; case where the spot diameter B of the measurement region $R_D$ is larger than the spot diameter A of the illumination region $R_L$ and the measurement region $R_D$ is moved, as illustrated in FIGS. 5 and 6.

Specifically, the spot diameter B of the measurement region $R_D$ has a size of 2d (two times the acceptable fluctuation amount d) or more greater than the spot diameter A of the illumination region $R_L$, that is, satisfies the following formula (1).

$$B \geq A + 2d \tag{1}$$

Therefore, the illumination region $R_L$ is included inside the measurement region $R_D$ even in a case where the position of the medium M with respect to the spectrometer 17 is moved to the first position P1 or the second position P2, as illustrated in FIGS. 5 and 6.

Figure 9:
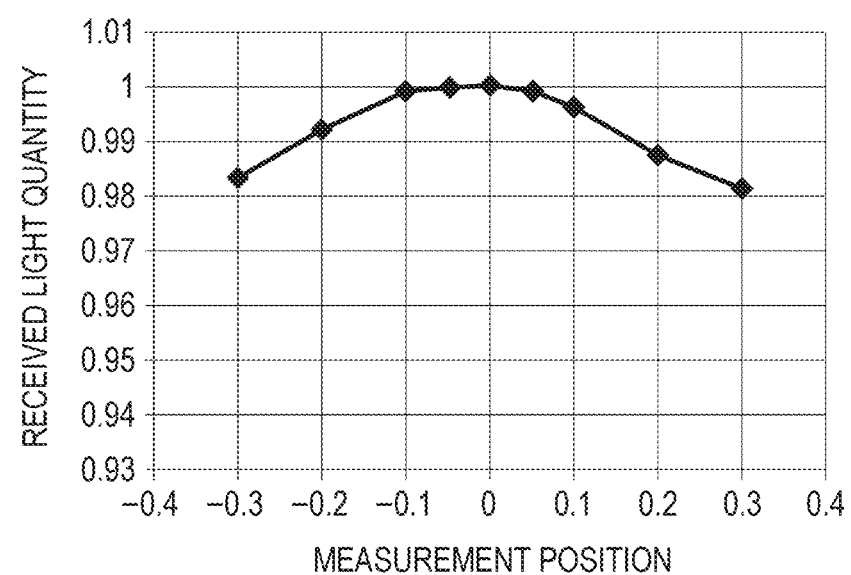
FIG. 9 is a drawing illustrating the total light quantity of light received by the light receiving unit of the measurement unit with respect to the position of the measurement region in the first embodiment.

FIG. 9 is a drawing illustrating the total light quantity of light received by the light receiving unit 172B of the measurement unit 172 with respect to the position of the measurement region $R_D$ in the embodiment.

As illustrated in FIG. 9, it is found that a lowering of the total light quantity of the measurement light received by the light receiving unit 172B is suppressed by the movement of the measurement region $R_D$ in the embodiment.

It is possible to set the measurement region $R_D$ and the illumination region $R_L$ by means of the illumination optical member 171B of the light source unit 171 or the light receiving optical member 172D of the measurement unit 172, as described above.

For example, in a case of using a plurality of apertures and a collimator lens as the illumination optical member 171B, illumination light from the light source 171A is made parallel light by the collimator lens, and the opening diameter of the aperture is the spot diameter A of the illumination region $R_L$. Accordingly, illumination light that is the spot light on the illumination region $R_L$ with the spot diameter A can be radiated on the medium M.

In the light receiving optical member 172D, the light receiving optical member 172D is provided so that the point at which the main light beam of the illumination light and the medium M intersect at the reference position P0 is the reference center point O and the axis that is 45° from the reference center point O in the X direction and the Z direction matches the main light beam of the measurement light. In a case of using a plurality of apertures as the light receiving optical member 172D, the opening diameter of the apertures is $B/2^{1/2}$. Accordingly, the measurement light from the measurement region $R_D$ can be received by the light receiving unit 172B.

Actions and Effects of the Embodiment

The printer 10 of the embodiment is provided with a spectrometer 17 on the carriage 13 and the spectrometer 17 is provided with a light source unit 171 and a measurement unit 172. The measurement region $R_D$ of the medium M by the measurement unit 172 is a range that is larger than the illumination region $R_L$ of the illumination light radiated from the light source unit 171 to the medium M and the illumination region $R_L$ is included inside the measurement region $R_D$. That is, the light receiving optical member 172D of the measurement unit 172 guides measurement light from the measurement region $R_D$ that is larger than the illumination region $R_L$ and inside which the illumination region $R_L$ is included even in a case in which the medium M is moved to the light receiving unit 172B.

Therefore, even in a case where the position of the medium M is displaced in the Z direction due to cockling or the like, the total light quantity of the measurement light incident on the measurement unit 172 (light receiving unit 172B) does not fluctuate by positioning the illumination region $R_L$ in the measurement region $R_D$ even in a case where the carriage 13 is displaced along the Z direction. Accordingly, it is possible to perform high precision measurement even in a case where fluctuations in the position of the measurement object arise due to cockling or the like.

In the embodiment, the direction of the illumination light and the direction of the measurement light are different in the spectrometer 17, and specifically, colorimetry is performed according to the 0/45° colorimetry system.

In this case, the optical geometric conditions stipulated by the colorimetry standard (JIS Z 8722) are achieved and it is possible to suppress defects that lower the measurement precision by specular reflection components reflected by the medium M being reflected in the measurement unit 172.

In the embodiment, the spot diameter B of the measurement region $R_D$ has dimensions two times the acceptable fluctuation amount d or more larger than the spot diameter A of the illumination region $R_L$. Therefore, in a case where the distance between the medium M and the spectrometer 17 is within a range of the acceptable fluctuation amount d from the reference distance, the illumination region $R_L$ is included within the measurement region $R_D$. Therefore, even in a case where distance fluctuations between the medium M and the spectrometer 17 arise as described above, it is possible to suppress fluctuations in the total light quantity of the measurement light incident on the light receiving unit 172B, and improvements in the measurement precision are achieved.

In the embodiment, the measurement unit 172 is provided with a spectral device 172A, and light divided by the spectral device 172A is received by the light receiving unit 172B. Therefore, it is possible to carry out spectroscopic measurement with respect to the measurement region $R_D$ of the medium M. Since the chromaticity and the like of the image formed on the medium M can be precisely calculated, it is possible to carry out calibration of the printing unit 16 with high precision based on the spectroscopic measurement results or the calculated chromaticity.

The variable wavelength interference filter 5 is used as the spectral device 172A. The variable wavelength interference filter 5 has a simple configuration in which a pair of reflection films 54 and 55 face one another, and low costs and size reductions are possible compared to a case of using another spectral element such as an AOTF or an LCTF, and it is possible to reduce the size of the measurement unit 172. Thus, the measurement unit 172 is easily mounted to the carriage 13, and it is also possible to suppress defects, such as the movement of the carriage 13 being impeded by the weight of the measurement unit 172.

Since the spectrometer 17 is mounted on the carriage 13 in addition to the printing unit 16, simplification of the configuration is achieved compared to a case of using a carriage for the printing unit 16 and using a carriage for the spectrometer 17. It is possible to immediately carry out colorimetry on the formed image using the measurement unit 172 after the image formation (printing) on the medium M by the printing unit 16 by being able to mount both the printing unit 16 and the spectrometer 17 on the carriage 13. Although there are cases of cockling arising in the medium M due to ink not drying immediately after printing by the printing unit 16, in the embodiment, it is possible to suppress a lowering of the measurement precision due to cockling as described above.

In the embodiment, the spectrometer 17 is mounted in the printer 10 provided with a printing unit 16 that forms an image on the medium M, and carries out spectroscopic measurement with respect to the medium M. The calibration unit 154E refreshes the printing profile data based on the reflectivity or chromaticity of each measurement wavelength calculated from the spectroscopic measurement results.

In the printer 10, it is possible to carry out spectroscopic measurement with high precision on a color patch as described above, and possible to perform a colorimetry process with high precision. Accordingly, it is possible to form an image in which chromaticity desired by a user is reproduced with high precision by the printing unit by refreshing the printing profile data based on the colorimetry results of the colorimetry process.

Second Embodiment

Next, the second embodiment according to the invention will be described.

In the above-described first embodiment, a configuration in which the illumination region $R_L$ and the measurement region $R_D$ are circular was described as an example. In contrast, the second embodiment differs from the first embodiment on the feature of the measurement region $R_D$ being elliptical.

Figure 10:
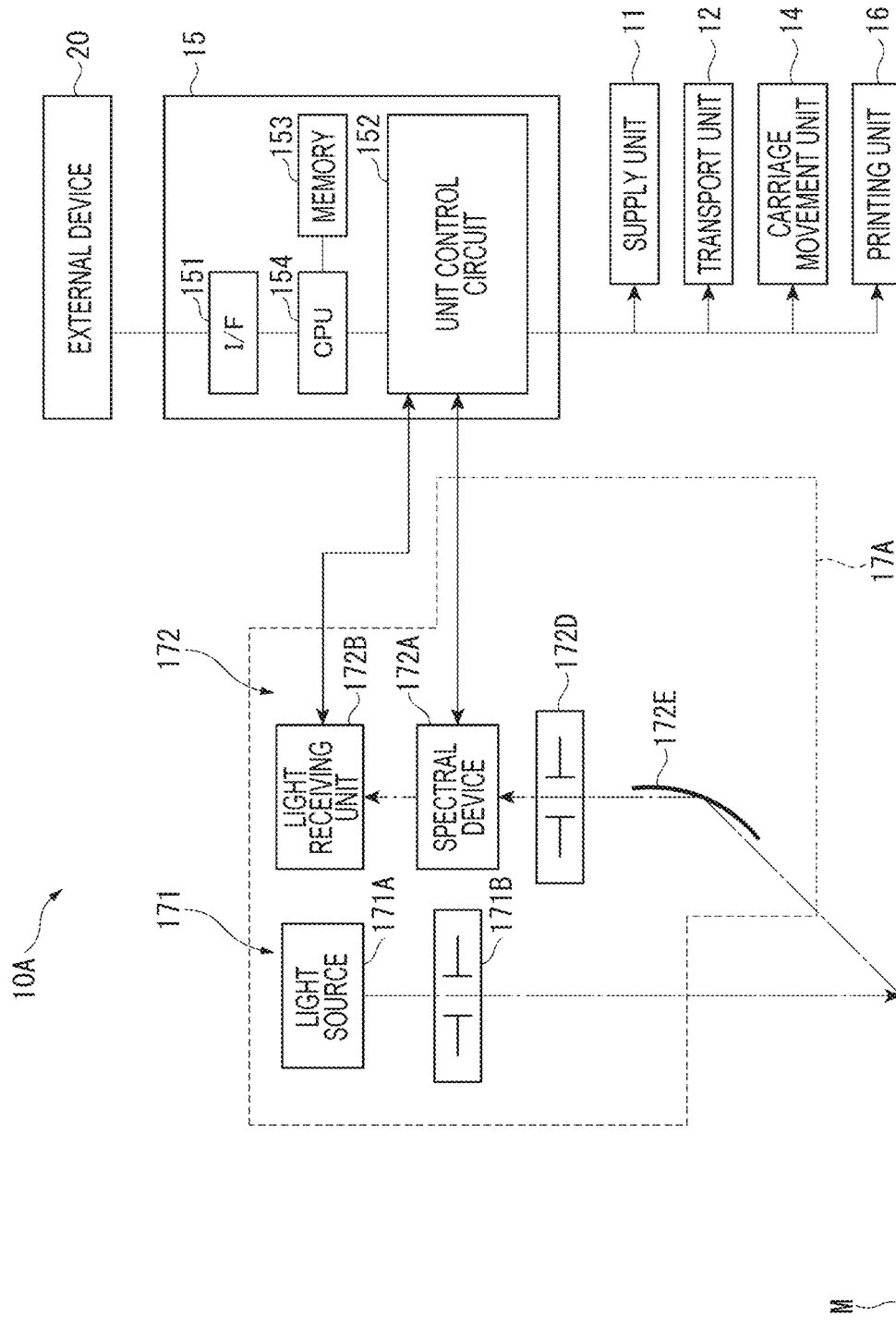
FIG. 10 is a block diagram illustrating a schematic configuration of the printer of the second embodiment.

FIG. 10 is a drawing illustrating the schematic configuration of the second embodiment according to the invention. It should be noted that in the following description, matters already described are given the same reference numerals and description thereof will be omitted or simplified.

As illustrated in FIG. 10, the printer 10A of the second embodiment is provided with a supply unit 11, a transport unit 12, a carriage 13, a carriage movement unit 14, and a control unit 15, similarly to the first embodiment. The carriage 13 includes a printing unit 16 and a spectrometer 17A similarly to the first embodiment.

Here, the spectrometer 17A of the embodiment has a concave mirror 172E disposed instead of the reflecting mirror 172C of the first embodiment in the measurement unit 172.

The concave mirror 172E includes a curvature that guides light from the elliptical measurement region $R_D$ on the medium M to the light receiving unit 172B.

Figure 11:
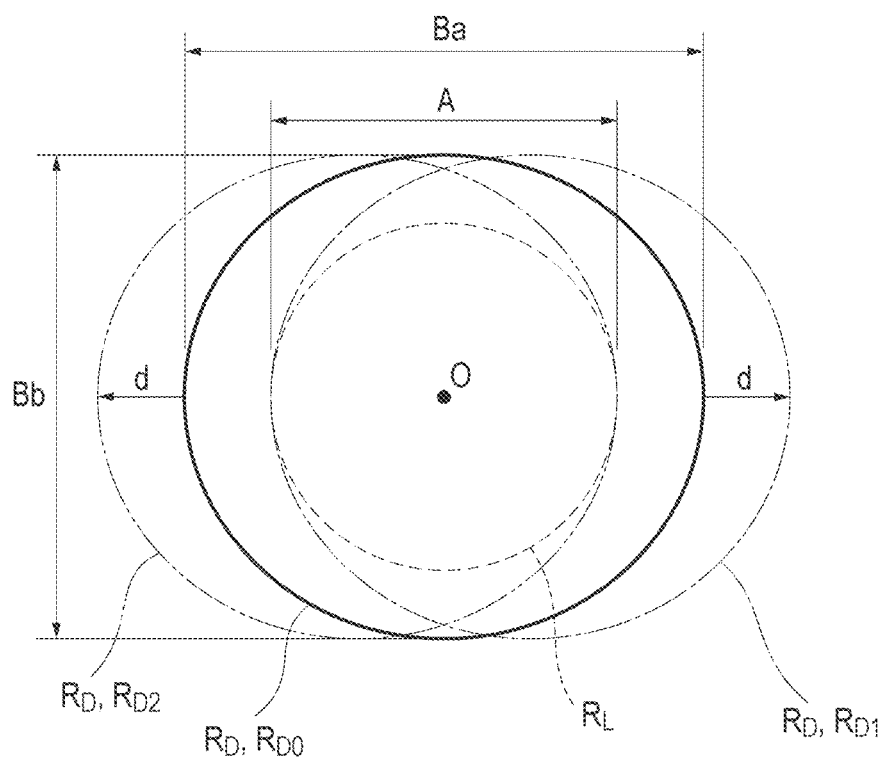
FIG. 11 is a drawing illustrating a positional relationship of the measurement region and the illumination region when the medium is viewed from the normal direction in the second embodiment.

FIG. 11 is a drawing illustrating the positional relationship between the measurement region $R_D$ and the illumination region $R_L$ when the medium is viewed from the normal direction. The solid line in FIG. 11 is the measurement region $R_D$ ($R_{D0}$) in a case where the distance between the medium M and the spectrometer 17A is the reference distance (case where the medium M is positioned at the reference position P0). The dashed line is the measurement region $R_D$ ($R_{D1}$) in a case where the distance between the medium M and the spectrometer 17A is smaller than the reference distance by the acceptable fluctuation amount d (case where the medium M is positioned at the first position P1). The dashed line is the measurement region $R_D$ ($R_{D2}$) in a case where the distance between the medium M and the spectrometer 17A is greater than the reference distance by the acceptable fluctuation amount d (case where the medium M is positioned at the second position P2).

As illustrated in FIG. 11, the measurement region $R_D$ in the embodiment is an ellipse. Specifically, the measurement region $R_D$ is an ellipse with the long axis in the direction in which the measurement region $R_D$ moves according to the fluctuations in the distance between the medium M and the spectrometer 17A.

It should be noted that the example illustrated in FIG. 11 is an example in which the end portion on the −X side of the measurement region $R_D$ contacts the end portion on the −X side of the illumination region $R_L$ ($R_{D1}$) when the medium M is positioned at the first position P1 and the end portion on the −X side of the measurement region $R_D$ contacts the end portion on the −X side of the illumination region $R_L$ ($R_{D2}$) when the medium M is positioned at the second position P2 in a case where the measurement region $R_D$ moves in the X direction according to fluctuations in the distance between the medium M and the spectrometer 17A. In this case, the spot diameter of the illumination region $R_L$ is A, the acceptable fluctuation amount of the medium M is d, satisfying the following formula (2).

$$Ba \geq A + 2d \quad (2)$$

Meanwhile, as in FIG. 11, in a case where the measurement region $R_{D1}$ and the illumination region $R_L$ contact at the end portion on the −X side with respect to the first position P1 and the measurement region $R_{D2}$ and the illumination region $R_L$ contact at the end portion on the +X side with respect to the second position P2, the following formula (3) is satisfied.

$$A = Bb^2 / 4Ba \quad (3)$$

Thus, formula (3) is derived according to formulae (1) and (2), and the conditions Bb>0, Ba>0, A>0, and d>0.

$$2(A^2 + A \times d)^{1/2} \leq Bb < Ba \quad (4)$$

That is, in the embodiment, the concave mirror 172E able to form the measurement region $R_D$ that satisfies the formulae (1) and (3) is provided in the measurement unit 172.

Actions and Effects of the Embodiment

The measurement region $R_D$ in the embodiment is an ellipse. In this case, it is possible to make the area smaller compared to a case where the measurement region $R_D$ has a circular spot shape.

That is, in the first embodiment, it is necessary that the measurement region $R_D$ be circular and the spot diameter B thereof be B≥A+2d. In contrast, in the embodiment, the length dimension Ba of the long axis of the measurement region $R_D$ may be Ba≥A+2d as illustrated in formula (1). Accordingly, it is possible to make the area smaller compared to a case where the measurement region $R_D$ has a circular shape as described above. Thus, it is possible to suppress defects in which unnecessary reflection light from an unnecessary region on which the measurement light is not incident is incident on the measurement unit 172 and becomes stray light, and to achieve improvements in the measurement precision.

Modification Example of Second Embodiment

In the example illustrated in FIG. 11, although an example is given in which the end portions on the −X side of the measurement region $R_D$ and the illumination region $R_L$ contact one another when the medium M is positioned at the first position P1 and the end portions on the −X side of the measurement region $R_D$ and the illumination region $R_L$ contact one another when the medium M is positioned at the second position P2, the measurement region $R_D$ may be as illustrated in FIG. 12.

FIG. 12 is a drawing illustrating the positional relationship of the measurement region $R_D$ and the illumination region $R_L$ when the medium M is viewed from the normal direction in the modification example of the second embodiment.

In the example illustrated in FIG. 12, the measurement region $R_D$ ($R_{D1}$) contacts two points on the −X side of the circular illumination region $R_L$ when the medium M is positioned at the first position P1, and the measurement region $R_D$ ($R_{D2}$) contacts two points on the +X side of the illumination region $R_L$ when the medium M is positioned at the second position P2.

In this case, the length dimension Ba in the long axis direction of the measurement region $R_D$ is lengthened compared to the second embodiment; however, on the other hand, it is possible for the length dimension Bb in the short axis direction to be shortened.

Thus, high precision measurement in which the influence of stray light is suppressed can be carried out, similarly to the second embodiment.

Third Embodiment

Next, the third embodiment according to the invention will be described.

In the first embodiment, an example is illustrated in which the colorimetry process is carried out based on the colorimetry results measured by the measurement unit 172. In contrast, the embodiment differs from the first embodiment on the feature of the measurement results measured by the measurement unit being further corrected in response to the distance between the medium and the spectrometer, and the colorimetry process being carried out based on the correction results.

Figure 13:
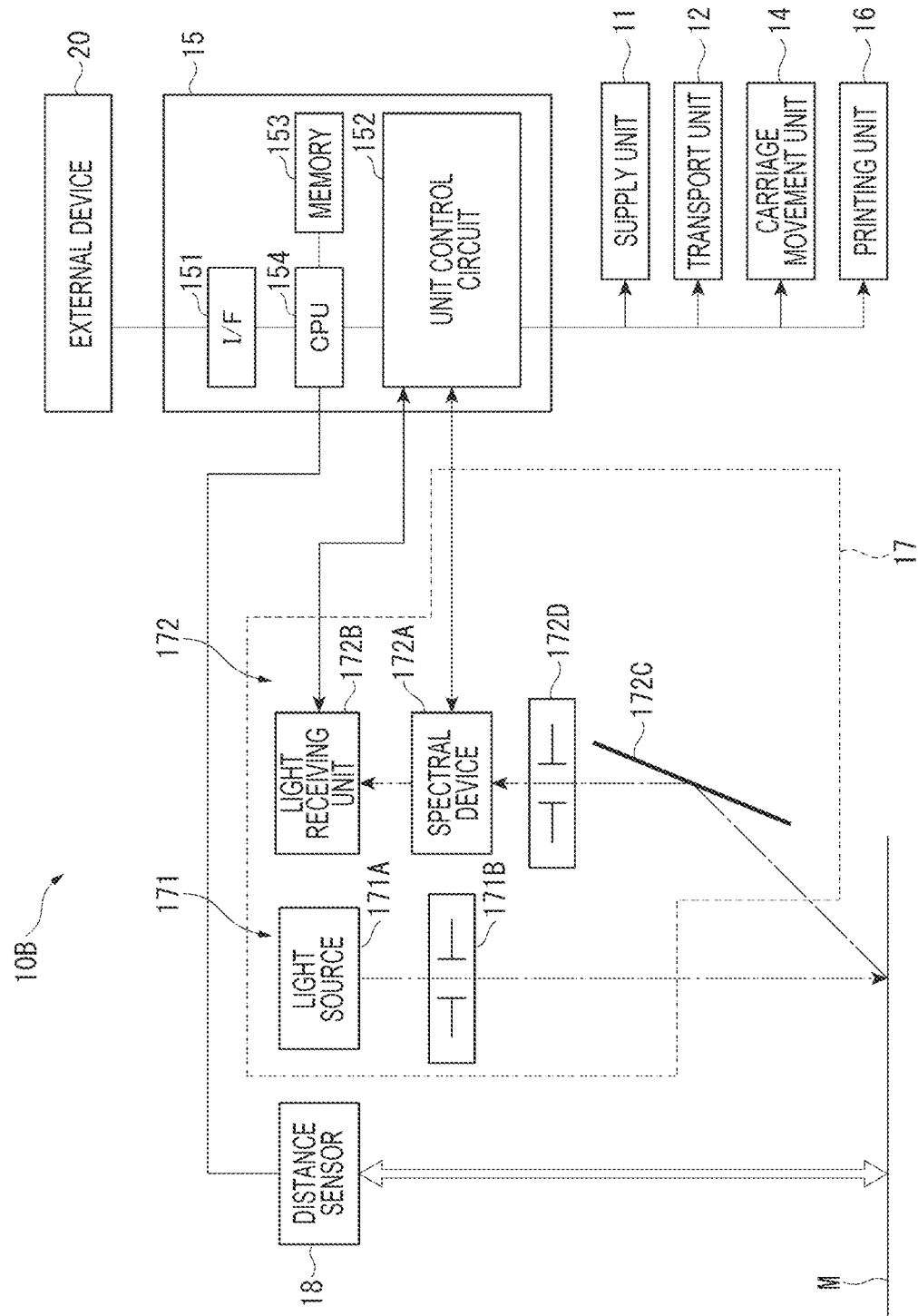
FIG. 13 is a diagram illustrating a schematic configuration of the printer of the third embodiment.

FIG. 13 is a block diagram illustrating a schematic configuration of the printer of the third embodiment.

In the embodiment, the printer 10B is provided with a supply unit 11, a transport unit 12, a carriage 13, a carriage movement unit 14, and a control unit 15, similarly to the first embodiment. In the embodiment, a distance sensor 18 is provided on the carriage 13 in addition to the printing unit 16 and the spectrometer 17, as illustrated in FIG. 13.

It should be noted that the shape of the measurement region $R_D$ may be circular as in the first embodiment, or may be elliptical as illustrated in the second embodiment or the modification example of the second embodiment.

The distance sensor 18 is a distance measurement unit of the invention and is provided with the printing unit 16 and the spectrometer 17 on the carriage 13.

Figure 14:
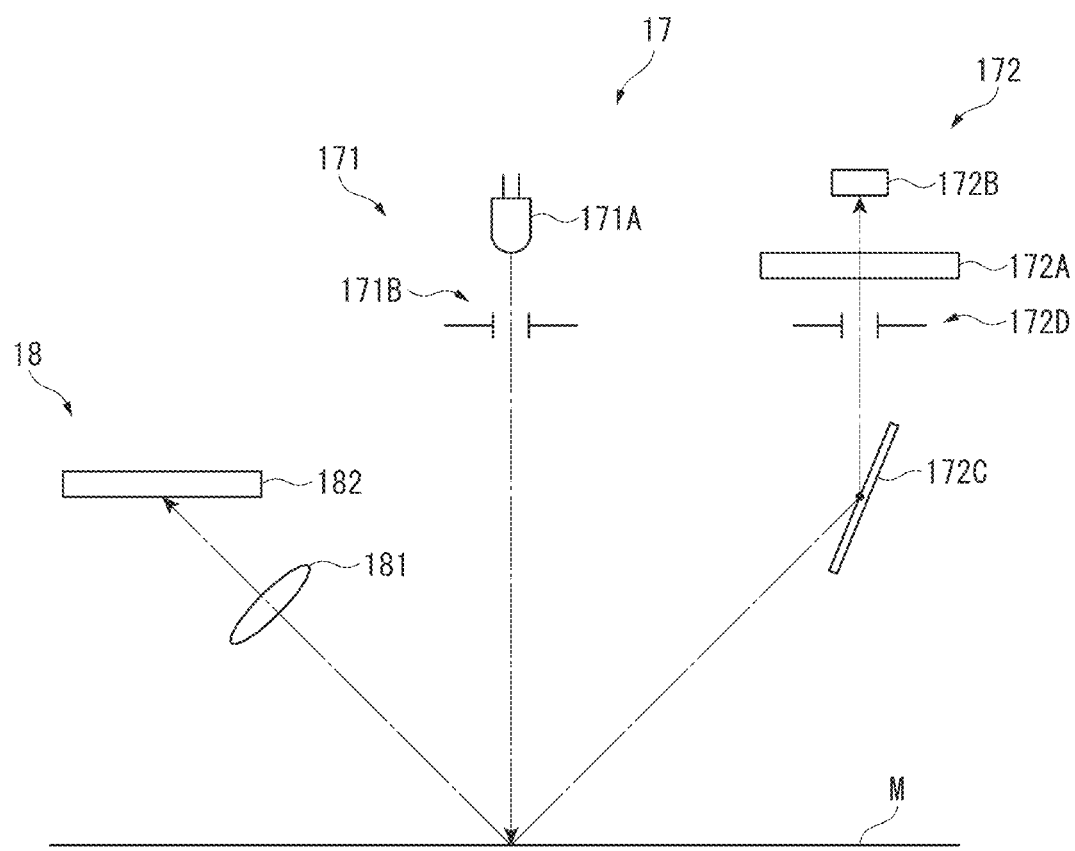
FIG. 14 is a block diagram illustrating a schematic configuration of a distance sensor of the third embodiment.

FIG. 14 is a block diagram illustrating a schematic configuration of the distance sensor 18 of the embodiment.

The distance sensor 18 is provided with a light receiving lens 181 and a position sensing device (PSD) 182, as illustrated in FIG. 14. The distance sensor 18 receives light incident from the medium M with the PSD 182 via the light receiving lens 181.

It should be noted that, in the embodiment, the PSD format distance sensor 18 that detects the center of mass of the received light, and calculates the distance between the medium M and the spectrometer 17 by means of trigonometry based on the center of mass is not limited thereto. For example, a complementary metal oxide semi-conductor-type (CMOS) distance sensor 18 or the like using a CMOS may be used. There is no limitation to a sensor that calculates the distance by means of trigonometry using the light from the light source 171A, and another distance measuring-type distance sensor may be used. For example, distance sensor or the like that separates laser light into a reference light and a measurement light and calculates the distance based on the interference patter of synthesized light in which the measurement light reflected by the medium M and the reference light are synthesized may be used.

The distance sensor 18 detects the distance between the medium M and the spectrometer 17 by receiving reflection light that is radiated onto the medium M from the light source unit 171 and reflected by the medium M, as illustrated in FIG. 14. That is, in the embodiment, the illumination light from the light source unit 171 is used for both spectroscopic measurement and distance measurement. In this case, the distance between the medium M and the spectrometer 17 is measured in the measurement region $R_D$ on which spectroscopic measurement is carried out by the spectrometer 17, even in a case where swelling due to cockling or the like arises in the medium M.

The distance-light quantity data is stored in the memory 153 in the control unit 15 of the embodiment. The distance-light quantity data is data indicating the relationship of the light quantity fluctuation amount in the measurement region $R_D$ with respect to the distance between the medium M and the spectrometer 17.

The colorimetry unit 154D measures the chromaticity with respect to the measurement region $R_D$ based on the amount of received light with respect to light with a plurality of wavelengths obtained by the spectroscopic measurement process, similarly to the first embodiment. In addition thereto, the colorimetry unit 154D of the embodiment functions as a correction unit of the invention, corrects the colorimetry results based on the distance measured by the distance sensor 18 and measures the chromaticity based on the corrected colorimetry results.

Method of Spectroscopic Measurement

Next, the method of spectroscopic measurement in the printer 10B of the embodiment will be described based on the drawings.

Figure 15:
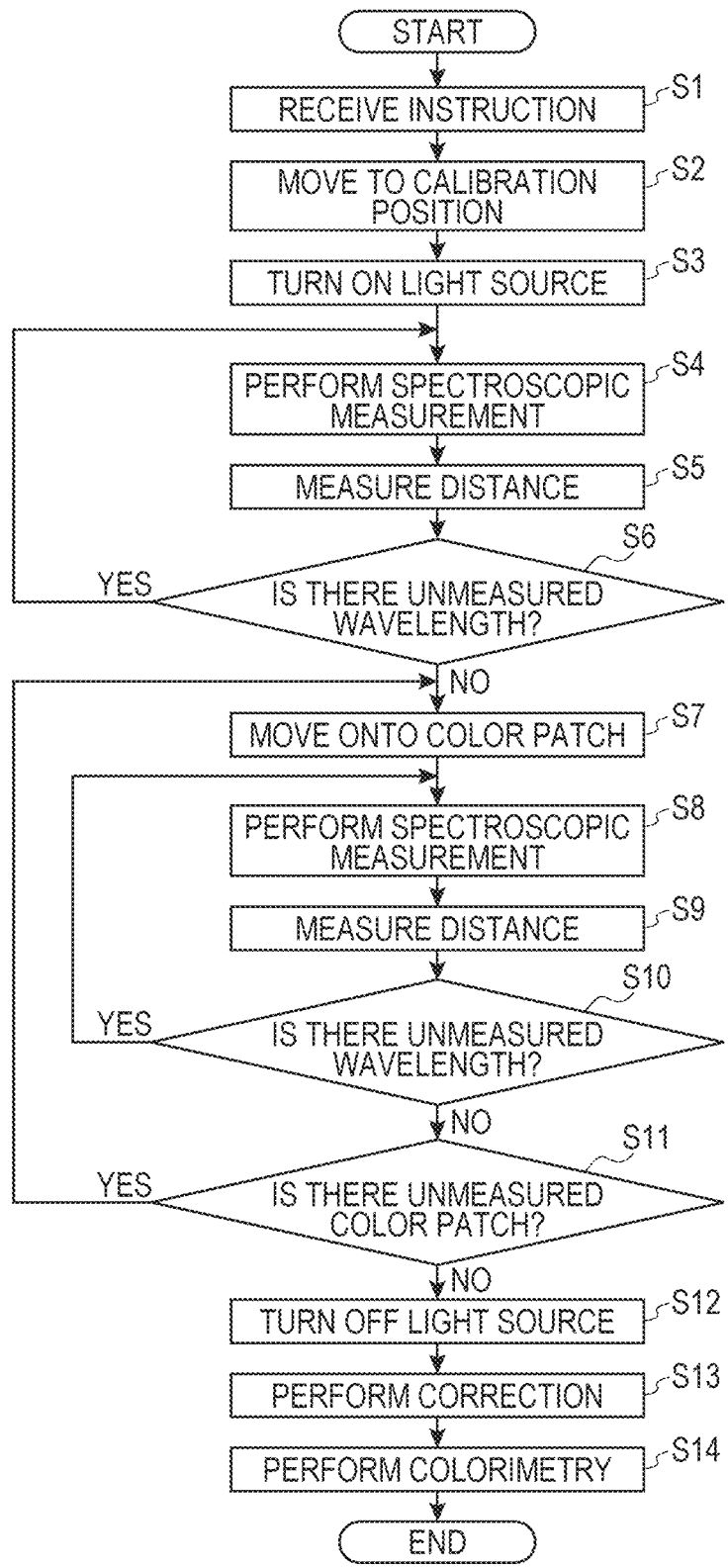
FIG. 15 is a flowchart illustrating a spectrometry method in the printer of the third embodiment.

FIG. 15 is a flowchart illustrating the method of spectroscopic measurement in the printer 10B.

Here, an example of carrying out the spectroscopic measurement process on the plurality of color patches printed by the printing unit 16 will be described as the spectroscopic measurement process by the printer 10B.

The spectroscopic measurement process of the example receives instructions to carry out the spectroscopic measurement process through a user operation or input from an external device 20 (step S1). Accordingly, the scanning control unit 154A controls the transport unit 12 and the carriage movement unit 14, causes the medium M to be moved in the Y direction so that the carriage 13 is positioned on a line on which the color patches are disposed, and further causes the carriage 13 to be moved to the calibration position (for example, end portion on the −X side) (step S2).

The calibration position is a position for carrying out the calibration data acquisition process, described later, and is a white region in which the color patches are not provided on the medium M (white sheet). The calibration reference material is not limited thereto, and a calibration reference material for which the reflectivity with respect to each wavelength is known may be separately installed. The white reference member for which the reflectivity is known may be installed on a portion of the platen 122 and the white reference member may be the calibration reference material of the invention.

Thereafter, the control unit 15 carries out the calibration data acquisition process that acquires the calibration data for correcting the spectroscopic measurement results. In the calibration data acquisition process, the measurement control unit 154C carries out the spectroscopic measurement process with respect to the correction position, and measures the light quantity (measured value in the invention that is output value from the light receiving unit 172B) of light with n bands (for example, 16 bands) of measured wavelengths that becomes 20 nm intervals in the visible light range of 400 nm to 700 nm Specifically, the measurement control unit 154C first causes the light source 171A to be turned on (step S3).

The measurement control unit 154C applies the driving voltage to the electrostatic actuator 56 of the variable wavelength interference filter 5 based on the V-λ data stored in the memory 153. Accordingly, the light with the measurement wavelength from the reflection light reflected from the medium M to the spectrometer 17 passes through according to the gap dimension of the reflection film 54 and 55 of the variable wavelength interference filter 5, is received by the light receiving unit 172B and the amount of received light with respect to the measurement wavelength is measured (step S4: spectroscopic measurement step).

The measurement control unit 154C acquires the distance between the medium M and the spectrometer 17 measured by the distance sensor 18 in synchronization with step S4 (step S5: distance measurement step).

The measurement control unit 154C stores the amount of received light (reference light quantity) measured in step S4 and the distance acquired in step S5 in association with the measurement wavelength (or driving voltage for the electrostatic actuator 56) in the memory 153.

Thereafter, the measurement control unit 154C determines whether there are unmeasured wavelengths (step S6). That is, the measurement control unit 154C determines whether the reference light quantity with respect to the 16 bands of measurement wavelengths with a 20 nm interval from 400 nm to 700 nm is measured. In a case where "Yes" is determined in step S6 (there are unmeasured wavelengths), the process returns to step S4 and the measurement of the reference light quantity with respect to the unmeasured wavelengths continues.

In a case where "No" is determined in step S6, the scanning control unit 154A controls the transport unit 12 and the carriage movement unit 14, and causes the carriage 13 to move so that the measurement region $R_D$ is positioned on the color patch (step S7).

The measurement control unit 154C carries out the same process as step S4 and carries out the spectroscopic measurement process with respect to the color patch. That is, the measurement control unit 154C applies a driving voltage to the electrostatic actuator 56 of the variable wavelength interference filter 5 based on the V-λ data stored in the memory 153, and measures the amount of received light based on the light reception signal from the light receiving unit 172B (step S8: spectroscopic measurement step).

The measurement control unit 154C acquires the distance between the medium M and the spectrometer 17 measured by the distance sensor 18 in synchronization with the acquisition timing of the amount of received light according to step S8 (step S9: distance measurement step).

The measurement control unit 154C stores the amount of received light (measurement light quantity) measured in step S8, and the distance acquired in step S9 in association with the measurement wavelength (or driving voltage for the electrostatic actuator 56) in the memory 153.

Thereafter, the measurement control unit 154C determines whether there are unmeasured wavelengths (steps S10) similarly to step S6, and in a case where "Yes" is determined, returns to step S8.

In a case where "No" is determined in step S10, the measurement control unit 154C further determines whether there are unmeasured color patches (step S11).

In a case where "Yes" is determined in step S11, the process returns to step S7, the scanning control unit 154A controls the transport unit 12 and the carriage movement unit 14, causes the measurement region $R_D$ in the spectrometer 17 to move to the next color patch, and continues the spectroscopic measurement process with respect to the next color patch.

In a case where "No" is determined in step S11, the measurement control unit 154C causes the light source 171A to be turned off (step S12).

Thereafter, the colorimetry unit 154D corrects the reference light quantity measured in step S4 and the measurement light quantity measured in step S8 based on the distance-light quantity data stored in the memory 153 (step S13: correction process).

Below, the light quantity correction by the colorimetry unit 154D will be described.

In the embodiment, similarly to the first embodiment, if the measurement region $R_D$ is larger than the illumination region $R_L$ and the distance between the medium M and the spectrometer 17 is within the acceptable fluctuation amount d with the reference distance as a center, the illumination region $R_L$ is included in the measurement region $R_D$. Therefore, it is possible to suppress fluctuations in the received light quantity incident (total light quantity received) on the light receiving unit 172B of the measurement unit 172, and high precision measurement results can be obtained. However, when the position of the measurement region $R_D$ is shifted from the reference position as illustrated in FIG. 9, the received light quantity lowers slightly.

In contrast, in the embodiment, the distance-light quantity data that indicates the changes in the amount of received light by the light receiving unit 172B with respect to the distance between the medium M and the spectrometer 17 is stored in the memory 153, and correction is carried out based on the distance-light quantity data.

Figure 16:
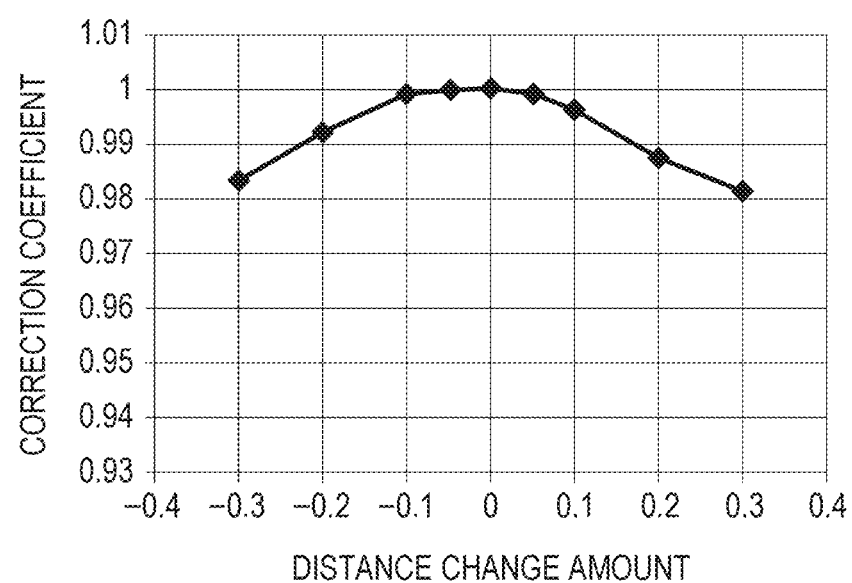
FIG. 16 is a drawing illustrating an example of distance-light quantity data in the printer of the third embodiment.

FIG. 16 is a drawing illustrating an example of distance-light quantity data in the embodiment.

Specifically, in the distance-light quantity data, the change ratio (below, may be referred to as correction coefficient) of the amount of received light by the light receiving unit 172B with respect to the change amount Δd (displacement amount in the Z direction from the reference position P0 of the medium M) of the distance between the medium M and the spectrometer 17 is stored in the distance between the medium M and the spectrometer 17, as illustrated in FIG. 16. The distance-light quantity data is provided for each measurement wavelength. Since spectroscopic measurement is carried out with respect to 16 bands of measurement wavelengths in the visible light range (400 nm to 700 nm) in the embodiment, distance-light quantity data is stored in the memory 153 for each of the 16 bands of measurement wavelengths.

It should be noted that, although FIG. 16 illustrates an example of distance-light quantity data in which the correction coefficient is recorded with respect to the distance change amount, the correction coefficient may be recorded for the distance between the medium M and the spectrometer 17.

In step S13, the colorimetry unit 154D acquires the correction coefficient (light quantity change rate) in response to the distance acquired by in step S5 from the distance-light quantity data, and calculates the correction reference amount in which the reference light quantity measured in step S4 is divided by the correction coefficient. Similarly, the correction coefficient is acquired in response to the distance acquired in step S8 from the distance-light quantity data, and the correction measurement light quantity in which the measurement light quantity measured in steps S9 is divided by the correction coefficient.

Thereafter, the colorimetry unit 154D calculates the reflectivity $R_\lambda$ according to $R_\lambda = E_\lambda / E_{\lambda,0}$ based on the correction reference light quantity ($E_{\lambda,0}$) with respect to each measurement wavelength and the correction measurement light quantity ($E_\lambda$) (step S14).

The colorimetry unit 154D calculates the chromaticity (for example, such as XYZ value or L*a*b* value) from the reflectivity $R_\lambda$ for each measurement wavelength and stores the result in the memory 153.

Furthermore, the colorimetry unit 154D may cause the calculated spectral reflectivity or chromaticity to be output and displayed on a display or the like provided in the external device 20 or printer 10, or control the printing unit 16, thereby printing the colorimetry results.

Thereafter, the calibration unit 154E refreshes the printing profile data stored in the memory 153 based on the colorimetry results of each color patch.

Actions and Effects of the Embodiment

The spectrometer 17 and the distance sensor 18 are mounted on the carriage 13 in the printer 10B of the embodiment. The colorimetry unit 154D uses the distance between the medium M and the spectrometer 17 measured by the distance sensor 18, and corrects the amount of received light with respect to each wavelength obtained by means of spectroscopic measurement using the spectrometer 17. Accordingly, since it is possible to correct the amount of received light in response to the distance even in a case where the distance between the medium M and the spectrometer 17 fluctuates, it is possible to carry out a high precision colorimetry process with respect to the color patch that is a measurement object based on the amount of received light.

In the embodiment, the distance sensor 18 measures the distance between the medium M and the spectrometer 17 using the illumination light from the light source 171A of the spectrometer 17. Therefore, it is possible to accurately measure the distance between the measurement region $R_D$ on the medium M and the spectrometer 17.

In the embodiment, the colorimetry unit 154D acquires the correction coefficient with respect to the measured distance based on the distance-light quantity data in which the fluctuation rate of the amount of received light (correction coefficient) by the light receiving unit 172B with respect to the distance between the medium M and the spectrometer 17 and corrects the amount of received light with the correction efficient. In the configuration, it is possible to easily correct the amount of received light based on the distance-light quantity data set in advance.

The distance-light quantity data is provided for each measurement wavelength, the colorimetry unit 154D corrects the amount of received light based on the distance-light quantity data in response to the measurement wavelength.

Accordingly, it is possible to precisely correct the amount of received light for each measurement wavelength, and it is possible for the colorimetry precision to be improved.

Fourth Embodiment

Next, the fourth embodiment according to the invention will be described.

In the first embodiment, an example in which the measurement region $R_D$ in the embodiment is larger size than the illumination region $R_L$ and the illumination region $R_L$ is included in the measurement region $R_D$ is illustrated. In contrast, the fifth embodiment differs from the first embodiment on the feature of the illumination region $R_L$ being larger than the measurement region $R_D$.

Figure 17:
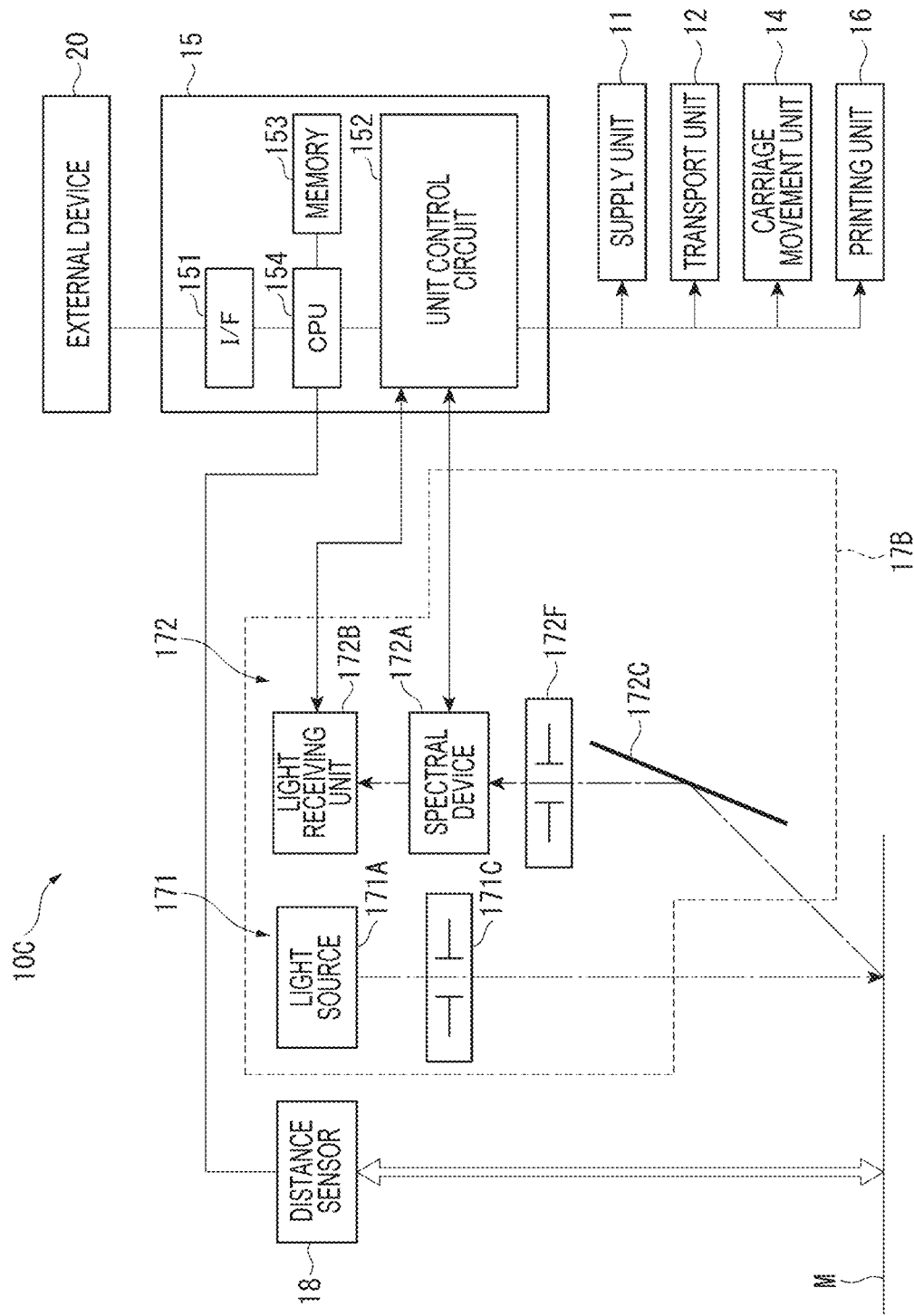
FIG. 17 is a block diagram illustrating a schematic configuration of the printer of the fourth embodiment.

FIG. 17 is a block diagram illustrating a schematic configuration of the printer 10C in the fourth embodiment.

As illustrated in FIG. 17, the printer 10C of the embodiment is provided with a supply unit 11, a transport unit 12, a carriage 13, a carriage movement unit 14, and a control unit 15, similarly to the third embodiment. And the carriage 13 includes a printing unit 16, a spectrometer 17B, and a distance sensor 18.

Figure 18:
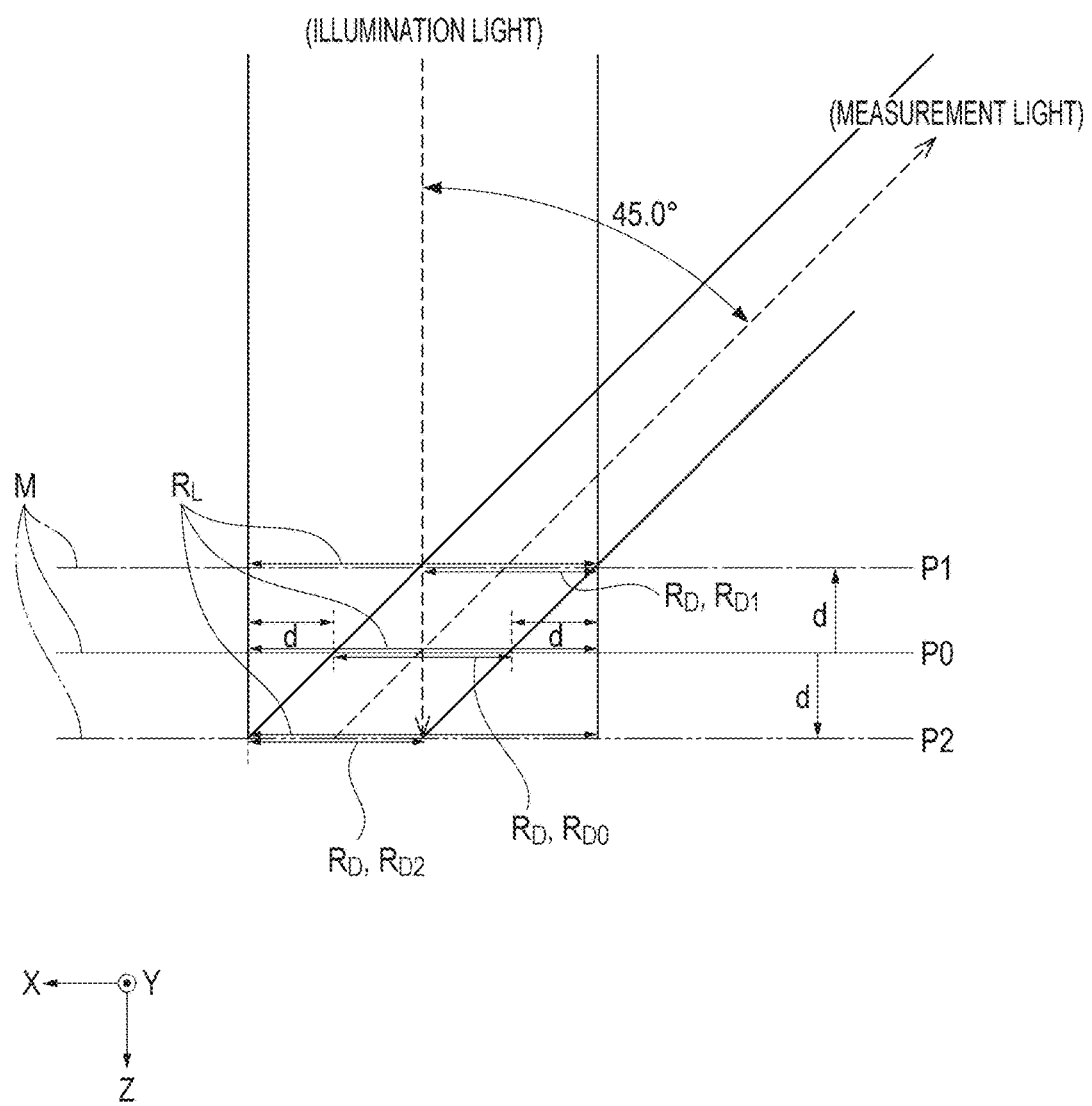
FIG. 18 is a drawing illustrating the position of the measurement region with respect to the illumination region on the XZ plane when the medium is displaced along the normal line in the fourth embodiment.

FIG. 18 is a drawing illustrating the position of the measurement region with respect to the illumination region on the XZ plane when the medium is displaced along the normal line in the fourth embodiment.

The illumination optical member 171C of the spectrometer 17B of the embodiment radiates measurement light on the illumination region $R_L$ as illustrated in FIG. 18, and the light receiving optical member 172F guides the measurement light from the measurement region $R_D$ as illustrated in FIG. 18 to the light receiving unit 172B.

That is, in the embodiment, the illumination region $R_L$ is larger than the measurement region $R_D$ and the measurement region $R_D$ is included in illumination region $R_L$. Specifically, the spot diameter A of the illumination region $R_L$ and the spot diameter B of the measurement region $R_D$ satisfy the following formula (5) using the acceptable fluctuation amount d. That is, in the embodiment, the illumination optical member 171C and the light receiving optical member 172F that satisfy the formula (5) are provided.

$$A \geq B + 2d \quad (5)$$

Although an example in which the illumination region $R_L$ and the measurement region $R_D$ is circular is illustrated in the embodiment, there is no limitation thereto. For example, the illumination region $R_L$ may be an ellipse in which the movement direction of the measurement region $R_D$ is the long axis. In this case, in a case where the length dimension of the long axis of the illumination region $R_L$ is Aa and the spot diameter of the measurement region $R_D$ is B, the following formula (6) is satisfied, and in a case where the length direction of the short axis of the illumination region $R_L$ is Ab, the illumination optical member 171C and the light receiving optical member 172F may be designed to satisfy the following formula (7).

$$Aa \geq B + 2d \quad (6)$$

$$2(B^2 + B \times d)^{1/2} \leq Ab < Aa \quad (7)$$

The illumination optical member 171C of the embodiment is formed including an integrator optical system (for example, such as a fly eye lens) that uniformizes illumination unevenness of the illumination light. In this case, illumination light with a substantially uniform light quantity is radiated on the illumination region $R_L$. Accordingly, even in a case where the measurement region $R_D$ moves, the light quantity of the illumination light radiated on the measurement region $R_D$ becomes substantially the same light quantity, and fluctuations in the total light quantity of the measurement light received by the light receiving unit 172B are suppressed.

The distance sensor 18 is provided in the embodiment, similarly to the third embodiment, the colorimetry unit 154D corrects the measurement results (amount of received light) by the spectrometer 17B based on the distance-light quantity data stored in the memory 153.

In the embodiment, substantially uniform light is radiated on the illumination region $R_L$ by means of the integrator illumination optical system that forms the illumination optical member 171C. However, the influence of the light quantity fluctuations due to illumination unevenness in the illumination light strongly appears compared to the first to third embodiments. In contrast thereto, a lowering of the measurement precision due to the light quantity fluctuations as above can be suppressed by performing correction based on the distance measured by the distance sensor 18.

Actions and Effects of the Embodiment

In the embodiment, the illumination region $R_L$ of the measurement light radiated from the light source unit 171 to the medium M is larger than the measurement region $R_D$ measurable by the measurement unit 172, and the measurement region $R_D$ included in the illumination region $R_L$. The integrator optical system is included in the illumination optical member 171C of the light source unit 171, and suppresses the illumination unevenness in the illumination light. Therefore, in a case where the distance between the medium M and the spectrometer 17B fluctuates and the measurement region $R_D$ moves, it is possible to suppress the influence of illumination unevenness, and improvements in the measurement precision are achieved.

The colorimetry unit 154D corrects the measurement results in response to the distance between the medium M and the spectrometer 17 measured by the distance sensor 18, similarly to the third embodiment. Therefore, even in a case where the total light quantity of the measurement light received by the light receiving unit 172B fluctuates due to the influence of the illumination unevenness, it is possible to obtain high precision measurement results by means of the correction.

Fifth Embodiment

Next, the fifth embodiment according to the invention will be described.

In each of the embodiments, an example is given of the 0/45° colorimetry system in which illumination light is radiated onto the medium M from substantially the normal direction, and the measurement light reflected as substantially 45° is measured. In contrast, the embodiment differs from each of the above-described embodiments on the feature of using a 45/0° colorimetry system in which illumination light is radiated on the medium M at an angle of substantially 45°, and the measurement light reflected in substantially the normal direction from the medium M is measured.

Figure 19:
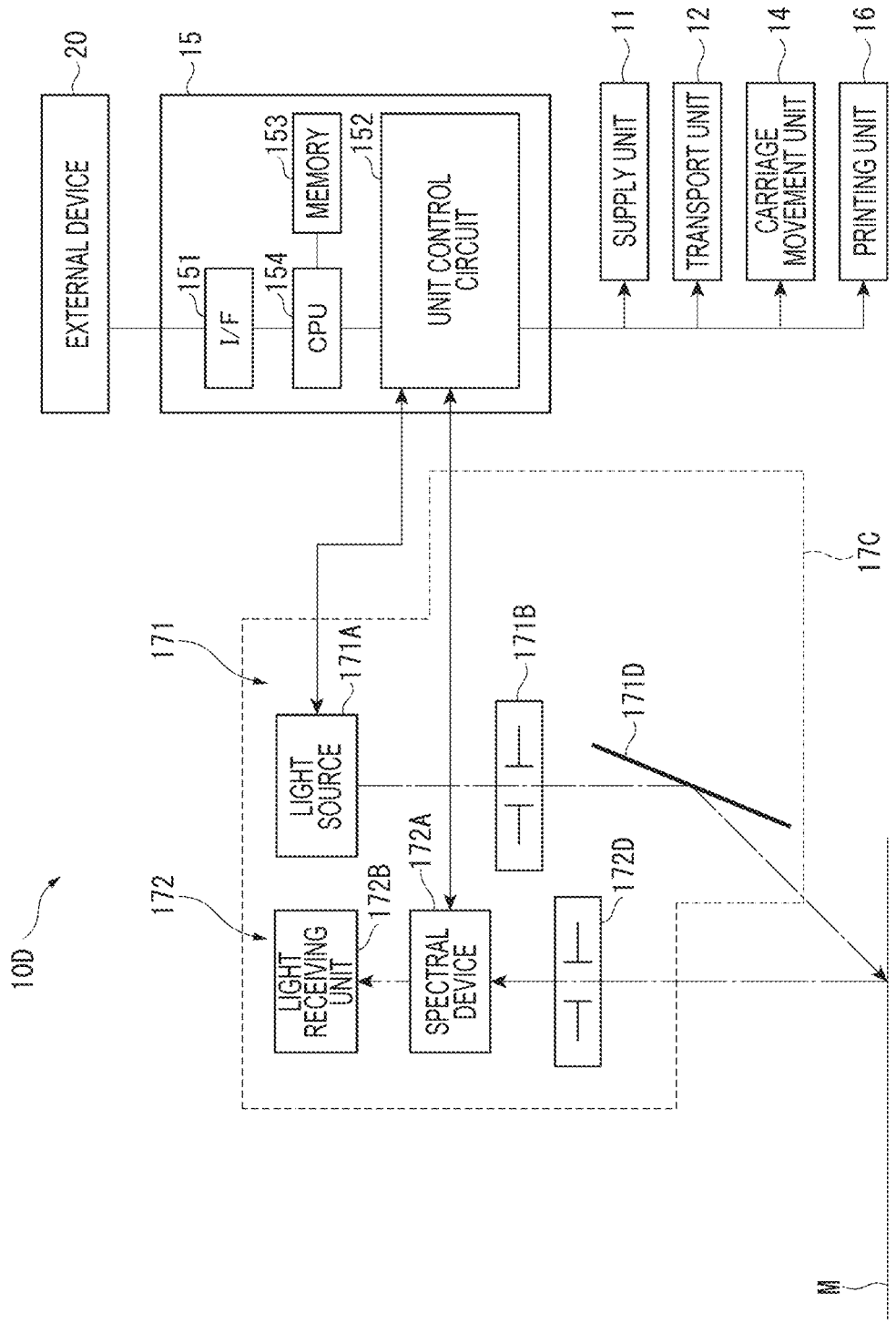
FIG. 19 is a block diagram illustrating a schematic configuration of the printer of the fifth embodiment.

FIG. 19 is a block diagram illustrating a schematic configuration of the printer 10D of the embodiment.

The printer 10D of the fifth embodiment is provided with a supply unit 11, a transport unit 12, a carriage 13, a carriage movement unit 14, and a control unit 15, similarly to the first embodiment. The carriage 13 includes the printing unit 16 and the spectrometer 17C.

The spectrometer 17C of the embodiment is formed including the light source unit 171 and the measurement unit 172 as illustrated in FIG. 19. The light source unit 171 includes the light source 171A, the illumination optical member 171B, and the reflecting mirror 171D, and the reflecting mirror 171D irradiates the medium M with the illumination light radiated from the light source 171A at an angle of 45°.

The measurement unit 172 is formed including the spectral device 172A, the light receiving unit 172B, and the light receiving optical member 172D, and measured the measurement light reflected in the normal direction by the medium M.

Figure 20:
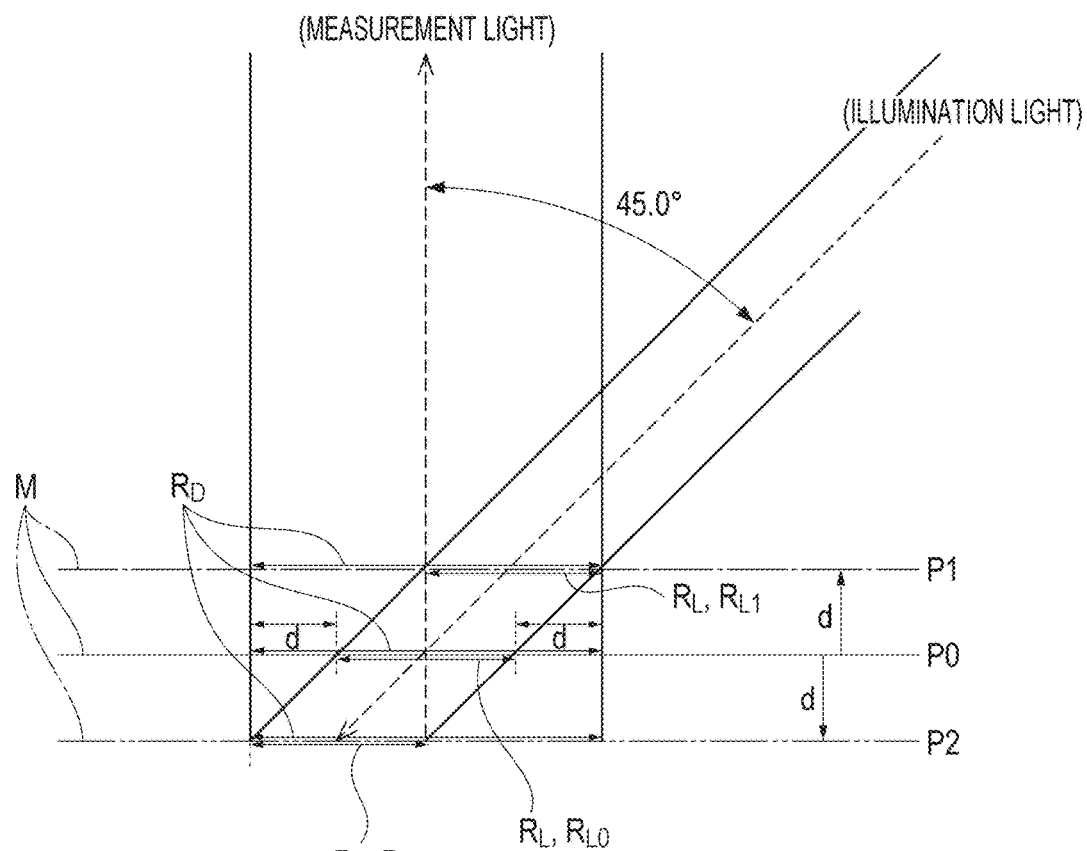
FIG. 20 is a drawing illustrating the position of the measurement region with respect to the illumination region on the XZ plane when the medium is displaced along the normal line in the fifth embodiment.

FIG. 20 is a drawing illustrating the position of the measurement region with respect to the illumination region on the XZ plane when the medium is displaced along the normal line in the fifth embodiment.

In the embodiment, when the position of the medium M moves from the reference position P0 (distance between the medium M and the spectrometer 17C fluctuates), the illumination region $R_L$ of the measurement light moves, as illustrated in FIG. 20. Here, in the embodiment, when the light source unit 171 and the measurement unit 172 is provided on a reference plane parallel to the platen 122, the straight line that connects the light source unit 171 and the measurement unit 172 becomes parallel to the X direction. Thus, when the position of the medium M moves from the reference position P0, the illumination region $R_L$ moves along the X direction.

Specifically, when reduced by the distance Δd between the medium M and the spectrometer 17C, the illumination region $R_L$ moves by Δd to the −X side. Meanwhile, when increased by the distance Δd between the medium M and the spectrometer 17, the illumination region $R_L$ moves by Δd on the +X side (side separating from the light source unit 171). Thus, when the medium M moves to the first position P1, the illumination region $R_L$ is the position ($R_{L1}$) moved by d from the position ($R_{L0}$) at the reference position to the −X side. Thus, when the medium M moves to the second position P2, the illumination region $R_L$ is the position ($R_{L2}$) moved by d from the position ($R_{L0}$) at the reference position to the +X side.

Thus, in a case where the medium M moves in a range within the acceptable fluctuation amount d with the reference position P0 as a center, in order to position the illumination region $R_L$ within the measurement region $R_D$, the relationship B≥A+2d is satisfied, similarly to the first embodiment, with the spot diameter of the illumination region $R_L$ as A, the spot diameter of the measurement region $R_D$ as B, and the acceptable fluctuation amount as d. That is, in the embodiment, the illumination optical member 171B and the light receiving optical member 172D that satisfy the above relational expression are provided.

Also in the fifth embodiment as described above, it is possible to exhibit the same actions and effects as the first embodiment.

Although an example in which the illumination region $R_L$ and the measurement region $R_D$ is circular is illustrated in the embodiment, there is no limitation thereto. For example, the measurement region $R_D$ may be an ellipse in which the movement direction of the illumination region $R_L$ is the long axis, similarly to the second embodiment and the modification example of the second embodiment. In this case, the above-described formulae (1) and (3) are not satisfied. In this case, the opening shape of the aperture that forms the light receiving optical member 172D may be elliptical, and a lens (or lens group) that collects measurement light from the elliptical measurement region $R_D$ on the light receiving unit 172B may be provided.

As illustrated in the third embodiment, a configuration may be used that is provided with the distance sensor 18, measures the distance between the medium M and the spectrometer 17C, and corrects the measurement results (amount of received light) with the measurement unit 172 in response to the measured distance.

Although the embodiment illustrates an example in which the measurement region $R_D$ is made larger than the illumination region $R_L$, a configuration may be used in which the illumination region $R_L$ is made larger than the measurement region $R_D$, and in which the measurement region $R_D$ is included in the illumination region $R_L$, as in the fourth embodiment, may be used.

OTHER EMBODIMENTS

It should be noted that the present invention is not limited to the above-described embodiments, and configurations obtained, as appropriate, according to modifications, improvements, and combinations of the embodiments within a scope capable of achieving the advantages of the invention are also included within.

For example, in the first to fourth embodiments, an example is provided of a 0/45° colorimetry system in which the illumination light is radiated from substantially the normal direction of the medium M, and the measurement light reflected as substantially 45° is measured by the measurement unit, and in the fifth embodiment, an example is provided of a 45/0° colorimetry system in which the illumination light is radiated from an angle of substantially 45° with respect to the medium M, and the measurement light reflected in substantially the normal direction of the medium M is measured by the measurement unit.

However, the invention is not limited to a colorimetry system according to the colorimetry standards as above, and it is possible to apply any colorimetry system in which illumination light is made incident at an arbitrary angle θ with respect to the normal line of the medium M and light that is reflected at an arbitrary angle φ or passes through the medium M is measured by the measurement unit.

Figure 21:
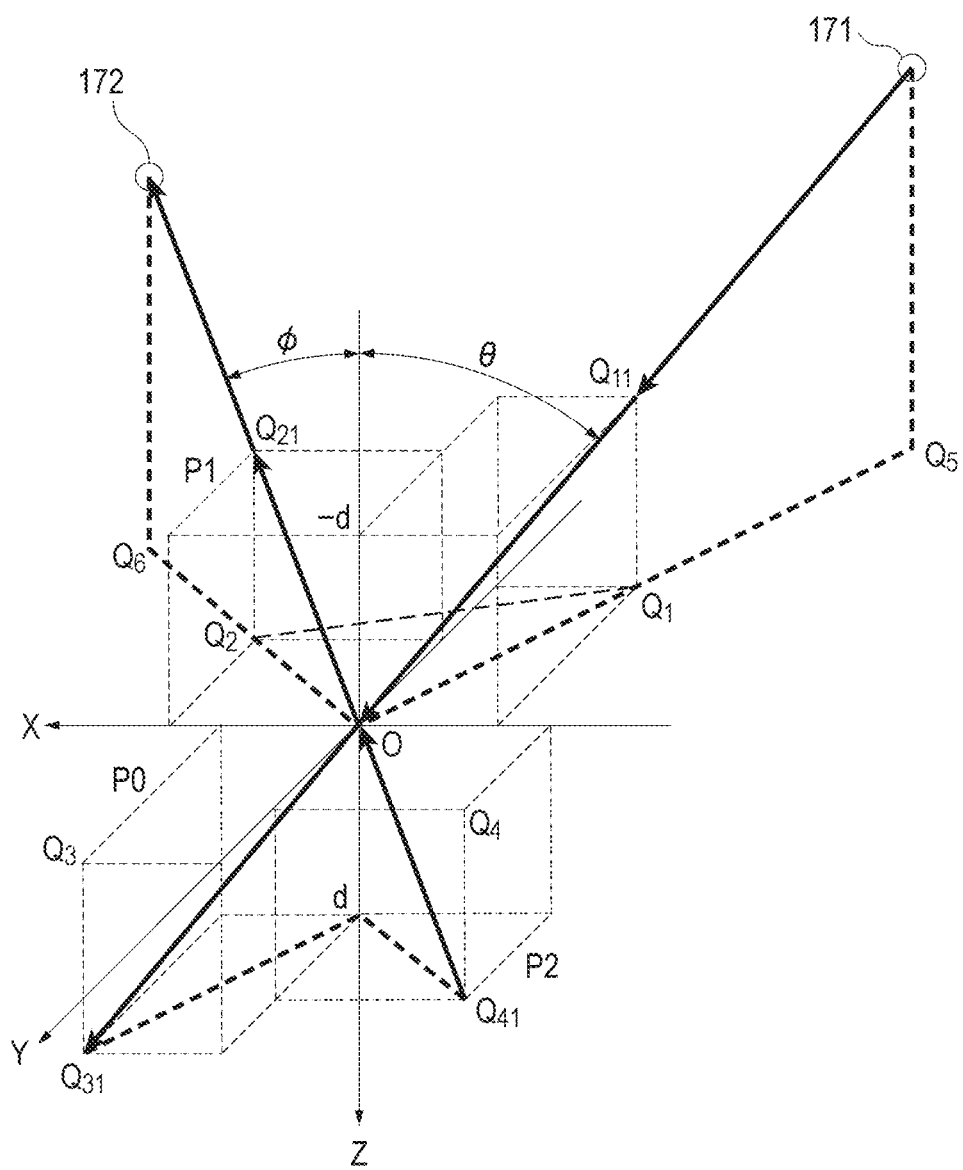
FIG. 21 is a drawing illustrating another embodiment and is a schematic view of a colorimetry model in which illumination light is incident from a light source unit at an angle θ with respect to the normal line of a medium, and the measurement light reflected at the angle φ with respect to the normal line of the medium is measured with the measurement unit.
Figure 22:
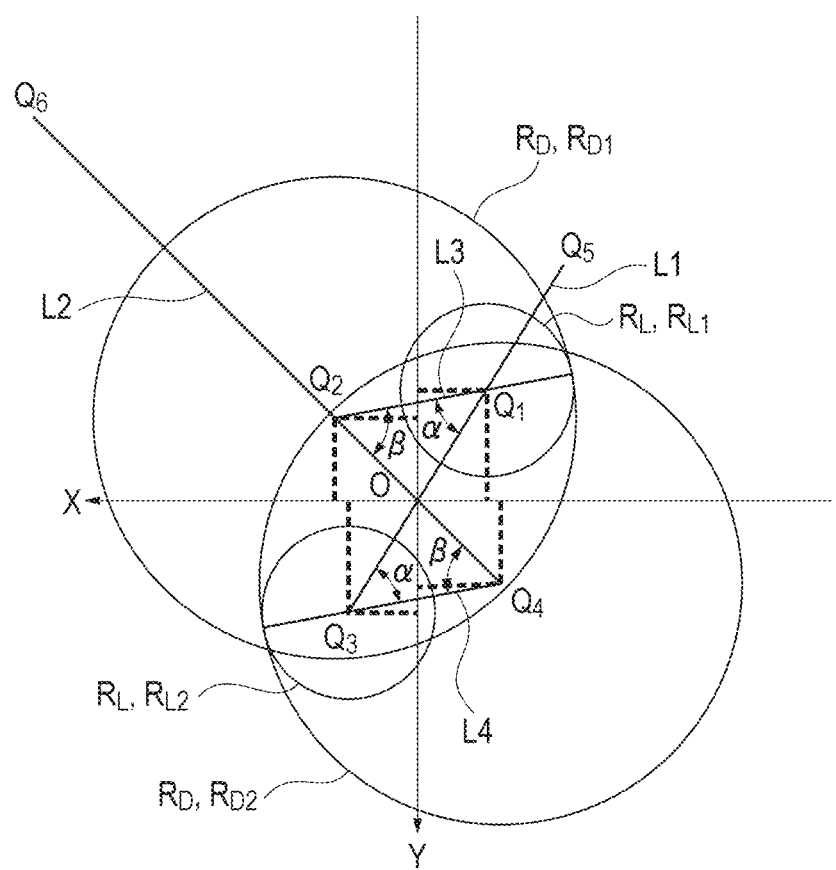
FIG. 22 is a drawing illustrating a movement range of the illumination region and the measurement region when

FIG. 21 is a schematic view illustrating a colorimetry model in which illumination light is incident from a light source unit at 171 an angle θ with respect to the normal line of a medium M, and the measurement light reflected at the angle φ with respect to the normal line of the medium M is measured by the measurement unit 172. FIG. 22 is a drawing illustrating a movement range of the illumination region $R_L$ and the measurement region $R_D$ when the colorimetry model in FIG. 21 is viewed from the normal direction of the medium M.

In FIG. 21, z=0 in a case where the medium M is positioned at the reference position P0, z=−d in a case where the medium M is moved to the first position P1 moved to the spectrometer 17 side by the acceptable fluctuation amount d, and z=d in a case where the medium M is moved to the second position P2 moved to the side receding from the spectrometer 17 by the acceptable fluctuation amount d. Here, from the planes parallel to the platen 122, the plane passing through z=0 (plane passing through the origin point and orthogonal to the normal line of the medium M) is referred to as the reference plane, the plane passing through z=−d as the first plane, and the plane passing through z=d as the second plane.

In FIG. 21, in a case where the medium M is positioned on the reference plane, the main light beam of the illumination light passes through the origin point 0, and the main light beam of the measurement light passes through the origin point 0. The point $Q_{11}$ is the point at which the main light beam of the illumination light contacts the first plane, the point $Q_{21}$ is the point at which the main light beam of the measurement light contacts the first plane, the point $Q_{31}$ is the point at which the main light beam of the illumination light contacts the second plane, and the point $Q_{41}$ is the point at which the main light beam of the measurement light contacts the second plane. The point $Q_1$ is a point (first point in the invention) at which the point $Q_{11}$ is projected on the reference plane, the point $Q_2$ is the point (second point in the invention) at which the point $Q_{21}$ is projected on the reference plane, the point $Q_3$ is the point at which the point $Q_{31}$ is projected on the reference plane, the point $Q_4$ is the point at which the point $Q_{41}$ is projected on the reference plane, the point $Q_5$ is the position (light source projection position in the invention) at which the light source unit 171 is projected on the reference plane, and the point $Q_6$ is the position (measurement unit projection position in the invention) at which the measurement unit 172 is projected on the reference plane. Only the points positioned on the reference plane are attached in FIG. 22.

In FIG. 22, the straight line that passes through the points $Q_5$, $Q_1$, O, and $Q_3$ is the straight line when the main light beam of the illumination light is projected on the reference plane, and is the first straight line L1 of the invention. The straight line that passes through the points $Q_6$, $Q_2$, O, and $Q_4$ is the straight line when the main light beam of the measurement light is projected on the reference plane, and is the second straight line L2 of the invention. The straight line passing through Q1 and $Q_2$ is the third straight line L3 of the invention. Furthermore, the straight line passing through points $Q_3$ and $Q_4$ is the fourth straight line L4.

In the example, the illumination region $R_L$ and the measurement region $R_D$ are circular, and the spot diameter of the illumination region $R_L$ is A and the spot diameter of the measurement region $R_D$ is B.

As illustrated in FIGS. 21 and 22, in a case where the medium M is with a range of ±d with the reference position as the center in the invention, the illumination region $R_L$ is included in the measurement region $R_D$. In a case where the size of the measurement region $R_D$ is made the smallest in such conditions, the illumination region $R_{L1}$ when medium M is positioned at the first position P1 is in internal contact with the measurement region $R_{D1}$, and the internal setting point is on the third straight line L3.

Here, because the length of the line segments $Q_1Q_{11}$ and $Q_2Q_{21}$ becomes d, the length of the line segment $OQ_1$ becomes d tan θ and the length of the line segment $OQ_2$ becomes d tan φ. Accordingly, the length of the line segment $Q_1Q_2$ becomes d(tan θ cos α+tan φ cos β).

Thus, the illumination optical member 171B of the light source unit 171 and the light receiving optical member 172D of the measurement unit 172 may be formed so that the measurement region $R_D$ and the illumination region $R_L$ that satisfy the following formula (8) are formed.

$$B \geq A + 2d(\tan \phi \cos \beta + \tan \theta \cos \alpha) \tag{8}$$

Although there are cases where the measurement region $R_D$ is circular in the above-described formula (8), the region may be elliptical as illustrated in the second embodiment and the modification example of the second embodiment.

Figure 23:
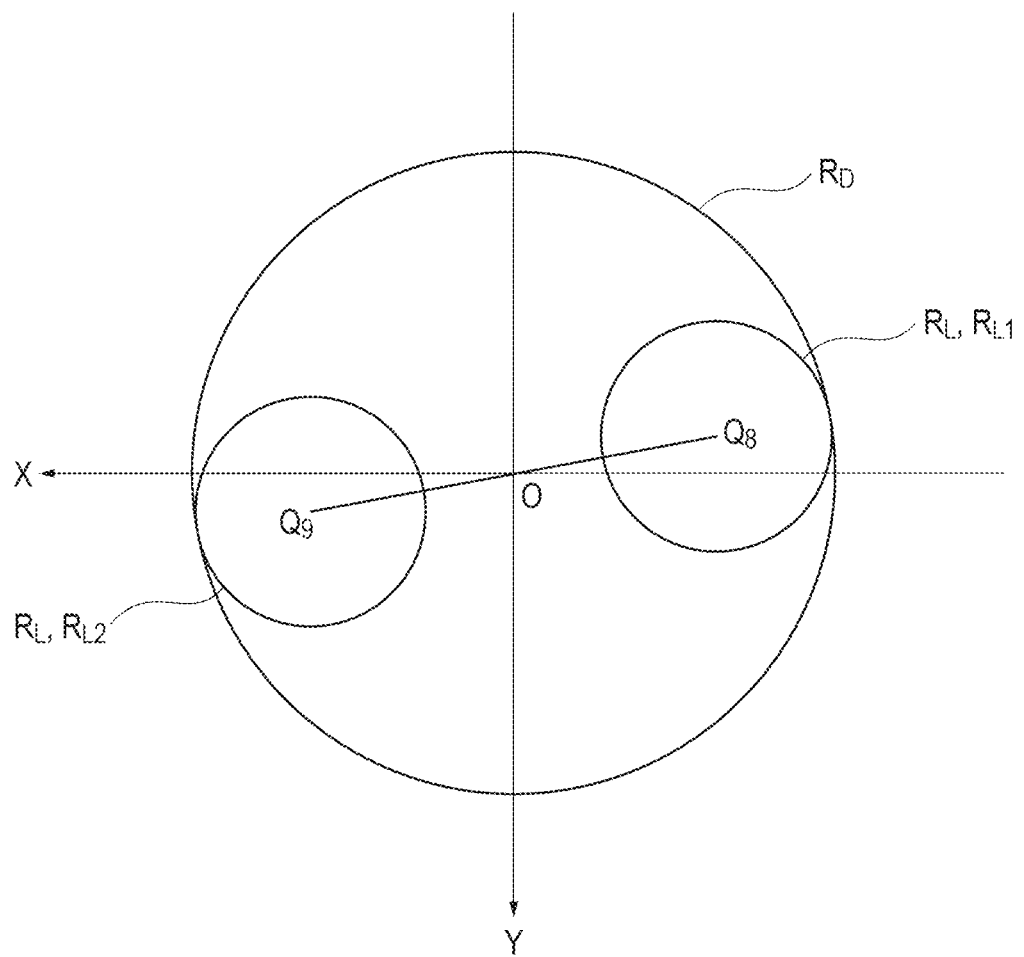
FIG. 23 is a drawing illustrating the relative position of the illumination region in FIG. 22 with respect to the measurement region.
Figure 24:
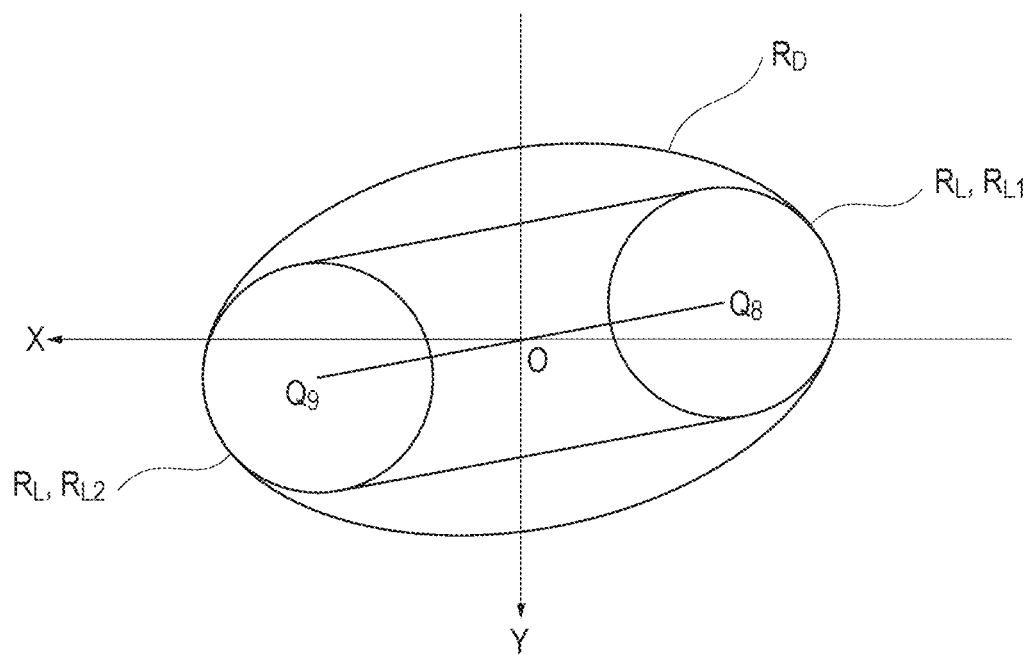
FIG. 24 is a drawing illustrating the long axis direction in a case where the measurement region is made an ellipse in the colorimetry model in FIG. 21.

FIG. 23 is a drawing illustrating the relative position of the illumination region $R_L$ in FIG. 22 with respect to the measurement region $R_D$. That is, the illumination regions $R_{L1}$ and $R_{L2}$ when the measurement region $R_{D1}$ with respect to the first position P1 and the measurement region $R_{D2}$ with respect to the second position P2 are combined are illustrated in FIG. 22. FIG. 24 is a drawing illustrating the long axis direction in a case where the measurement region $R_D$ is made an ellipse in the colorimetry model in FIG. 21.

As illustrated in FIG. 23, the illumination region $R_L$ moves relative to the measurement region $R_D$ following the line segment $Q_8Q_9$ from the illumination region $R_{L1}$ with respect to the measurement region $R_D$ when the medium M is positioned at the first position P1 as far as the illumination region $R_{L2}$ with respect to the measurement region $R_D$ when the medium M is positioned at the second position P2. Accordingly, the measurement region $R_D$ may cover the movement path on the line segment $Q_8Q9$ of the illumination region $R_L$.

Thus, in a case where the measurement region $R_D$ is elliptical, as illustrated in FIG. 24, the long axis of the measurement region $R_D$ may be made to match the direction of relative movement (straight line $Q_8Q_9$) with respect to the measurement region $R_D$ of the illumination region $R_L$.

It should be noted that although an example where the measurement region $R_D$ is elliptical is illustrated in the second embodiment and the modification example of the second embodiment and the colorimetry model in FIG. 24, there is no limitation thereto.

Figure 25:
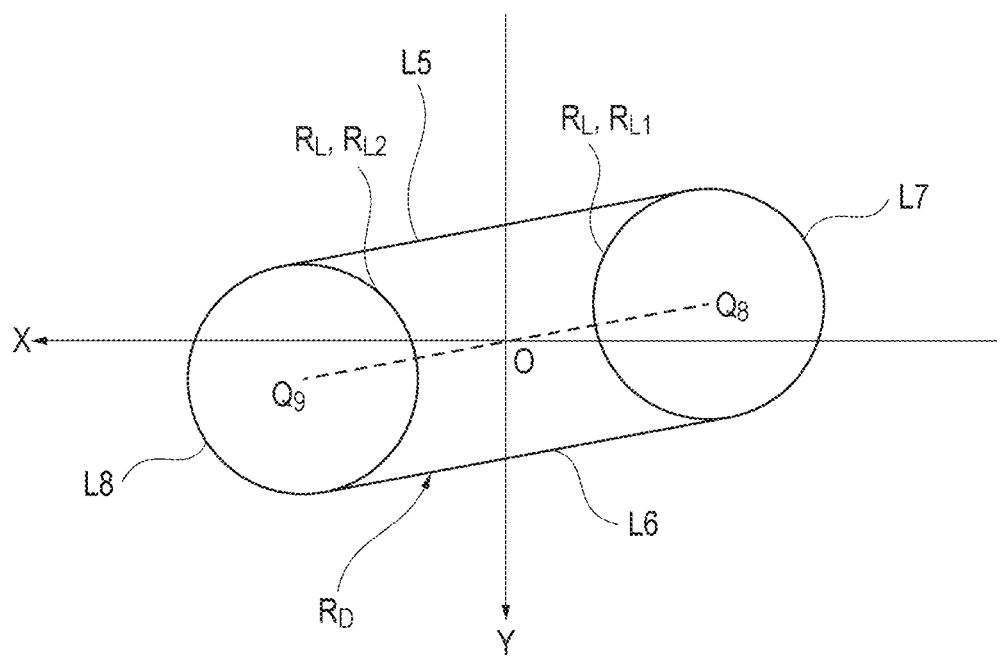
FIG. 25 is a drawing illustrating an example of another shape of the measurement region.

FIG. 25 is a drawing illustrating an example of another shape of the measurement region $R_D$. The example in FIG. 25 is an example with respect to the colorimetry model illustrated in FIG. 21.

That is, as illustrated in FIG. 25, the measurement region $R_D$ may be an oval (rounded rectangle) in which the direction of relative movement of the illumination region $R_L$ with respect to the measurement region $R_D$ is the long axis according to the distance fluctuations between the medium M and the spectrometer.

That is, the region surrounded by the two straight lines L5 and L6 separated by the distance A (spot diameter of the illumination region $R_L$)(path of relative movement of the illumination region $R_L$) in parallel to the line segment $Q_8Q_9$, the semicircle L7 with a diameter A that connects one end portion of the two straight lines L5 and L6 to one another, and the semicircle L8 with the diameter A that connects the other end of the two straight line(s) to one another is the measurement region $R_D$.

In this case, since the measurement region $R_D$ is larger than the illumination region $R_L$ and the illumination region $R_L$ is included in the measurement region $R_D$ when the medium M moves from the first position P1 as far as the second position P2, it is possible for the measurement precision to be improved, similarly to the first to third and fifth embodiments. In addition thereto, since the area of the measurement region $R_D$ can be made as small as possible, it is possible to minimize the influence of stray light, and further improvements in the measurement precision are achieved.

Although each embodiment and the modification example is an example of measuring the measurement light reflected by the medium M with a measurement unit, a configuration may be used that measures measurement light passing through the medium M with the measurement unit.

For example, the platen 122 is formed by a transparent member, and illumination light form the light source unit is radiated on a transparent or semi-transparent medium M from the rear side of the platen 122. Transmitted light that passes through the platen 122 and the medium M is received by the measurement unit 172 mounted on the carriage 13.

Even in this case, when the position in the Z direction of the medium M fluctuates in a case where light passing through in a direction of an angle $\phi$ with respect to the normal direction is received by the measurement unit, the position of the measurement region $R_D$ also moves. Thus, even in a case where the measurement region $R_D$ moves, it is possible to suppress fluctuations in the total light quantity of the measurement light incident on the measurement unit and improvements in the measurement precision are achieved, similarly to each embodiment and the modification example by setting the size of the measurement region $R_D$ so that the illumination region $R_L$ is included within the region thereof.

Although an example where the distance sensor 18 receives light that is radiated from the light source 171A and reflected by the medium M in the third and fourth embodiments, there is no limitation thereto.

For example, the distance between the medium M and the spectrometer 17 may be measured by providing a light source for sensor use for use by a separate distance sensor, radiating light from the light source for sensor use toward the medium M, and the reflection light being received by the distance sensor.

In the third and fourth embodiments, although the colorimetry unit 154D calculates the correction reference light quantity in which the reference light quantity is divided by the correction coefficient in response to the distance, calculates the correction measurement light quantity in which the measurement light quantity is divided by the correction coefficient in response to the distance and calculates the reflectivity based on the correction reference light quantity and the correction measurement light quantity, there is no limitation thereto. For example, the colorimetry unit 154D may calculate the reflectivity $R_\lambda$ using $R_\lambda = k_0 E_\lambda / k_1 E\lambda_0$ using the reference light quantity $E_{\lambda,0}$ and the measurement light quantity $E_\lambda$, where the correction coefficient with respect to the distance when the reference light quantity is measured is $k_{\lambda,0}$, and the correction coefficient with respect to the distance when the measurement light quantity is measured is $k_{\lambda,1}$.

In the embodiment, although the distance-light quantity data is provided with respect to each measurement wavelength, the colorimetry unit 154D acquires the correction coefficient from the distance-light quantity data according to the measurement wavelength, there is no limitation thereto. For example, the fluctuation rate in the total light quantity of the illumination light radiated from the light source 171A with respect to the distance (for example, displacement from the reference position P1) between the medium M and the spectrometer 17 may be recorded. In this case, one item of distance-light quantity data may be stored in the memory 153.

In each of the above-described embodiments, although an example of a configuration in which a unit control circuit 152 is provided in the control unit 15, each control unit may be provided in each unit separately to the control unit 15, as described above. For example, a configuration may be used in which a filter control circuit that controls the variable wavelength interference filter 5 in the spectrometer 17 and a light reception control circuit that controls the light receiving unit 172B are provided. A microcomputer or a storage memory in which the V-λ data is stored is built into the spectrometer 17, and the microcomputer may function as the measurement control unit 154C.

Although as example in which an ink jet printing unit 16 that causes ink supplied from the ink tank to be discharged by a piezoelectric element being driven is given as an example of a printing unit 16 in each of the above-described embodiments, there is no limitation thereto. For example, a configuration that generates air bubbles in the ink by means of a heater, thereby discharging ink or a configuration in which ink is discharged by an ultrasonic oscillator may be used as the printing unit 16.

It is possible to apply the invention to any printing type of printer such as s thermal printer using a heat transfer method, a laser printer, a dot impact printer, without being limited to the ink jet type.

In each of the above-described embodiments, although an example of a light transmissive type variable wavelength interference filter 5 through which light with a wavelength corresponding to the gap G between the reflection films 54 and 55 from the incident light is allowed to pass is given as the variable wavelength interference filter 5, there is no limitation thereto. For example, a reflection-type variable wavelength interference filter may be used by which light with a wavelength corresponding to the gap G between the reflection films 54 and 55 is reflected. Another type of variable wavelength filter may be used.

In each of the above-described embodiments, although an example in which a spectral device 172A in which the variable wavelength interference filter 5 is stored in the housing 6 is given, a configuration in which the variable wavelength interference filter 5 is direction provided in the spectrometer 17 may be used.

Although the variable wavelength interference filter 5 is given as an example of the spectral element, there is no limitation thereto. For example, a grating, AOTF, LCTF or the like may be used as the spectral element.

In each of the above-described embodiments, although an example of a configuration (rear spectrometry) in which the spectral device 172A provided with the variable wavelength interference filter 5 is provided in the measurement unit 172, there is no limitation thereto.

For example, a configuration (front spectrometry) in which a variable wavelength interference filter 5 or a spectral device 172A provided with a variable wavelength interference filter 5 is disposed in the light source unit 171, and that irradiates the medium M with light divided by the variable wavelength interference filter 5 may be used.

In each of the above-described embodiments, although an example of a printer 10 provided with a spectroscopic measurement device is given, there is no limitation thereto. For example, a spectroscopic measurement device that is not provided with the image forming unit and that carries out only the colorimetry process with respect to the medium M may be used. The spectroscopic measurement device of the invention may be incorporated in a quality inspection device that performs quality inspection on a printed matter than manufactured in a factory or the like, and in addition, the spectroscopic measurement device of the invention may be incorporated in any device.

Additionally, specific structures when carrying out the invention may be formed by combining, as appropriate, the embodiments and modification examples within a scope able to achieve the advantages of the invention, and or other structures and the like may be changed, as appropriate.

The entire disclosure of Japanese Patent Application No. 2015-212278, filed Oct. 28, 2015 is expressly incorporated by reference herein.

What is claimed is:

1. A measurement device, comprising:
   a light source that radiates an illumination light, the illumination light being reflected by a measurement object or passed through the measurement object so as to be a measurement light, the measurement light having a plurality of measurement wavelengths;
   a memory configured to store computer-readable instructions; and
   a processor configured to execute the computer-readable instructions so as to:
   cause a measurement unit to measure a light amount of the measurement light with respect to each of the plurality of measurement wavelengths;
   calculate reflectivity of the measurement light based on the light amount with respect to each of the plurality of measurement wavelengths; and
   calculate chromaticity based on the reflectivity of the measurement light with respect to each of the plurality of measurement wavelengths based on the reflectivity of the measurement light with respect to each of the plurality of measurement wavelengths,
   wherein one unit of a measurement region of the measurement object measurable by the execution of the processor is smaller than an entirety of an illumination region in which the measurement object is irradiated with the illumination light.

2. The measurement device according to claim 1, further comprising:
   a distance measurement unit that measures a distance between the measurement object and the measurement unit; and
   a correction unit that corrects a measured value measured by the execution of the processor based on the distance measured by the distance measurement unit.

3. The measurement device according to claim 2, wherein the correction unit acquires distance-light quantity data in which a light quantity fluctuation amount with respect to the distance between the measurement object and the measurement unit is recorded, and corrects the measured value based on the distance-light quantity data.

4. The measurement device according to claim 1, wherein the measurement unit includes a spectral element that divides the measurement light into a predetermined wavelength of the plurality of measurement wavelengths.

5. The measurement device according to claim 1, further comprising:
   a carriage on which the light source and the measurement unit are mounted; and
   a movement mechanism that causes the carriage to move relative to the measurement object.

6. A printing apparatus, comprising:
   the measurement device according to claim 1; and
   an image forming unit that forms an image on the measurement object.

7. A printing apparatus, comprising:
   the measurement device according to claim 2; and
   an image forming unit that forms an image on the measurement object.

8. A printing apparatus, comprising:
   the measurement device according to claim 3; and
   an image forming unit that forms an image on the measurement object.

9. A printing apparatus, comprising:
   the measurement device according to claim 4; and
   an image forming unit that forms an image on the measurement object.

* * * * *